United States Patent
Kwon et al.

(10) Patent No.: US 10,363,106 B2
(45) Date of Patent: Jul. 30, 2019

(54) SURGICAL ROBOT FOR STEREOTACTIC SURGERY AND METHOD FOR CONTROLLING STEREOTACTIC SURGERY ROBOT

(71) Applicant: KOH YOUNG TECHNOLOGY INC., Seoul (KR)

(72) Inventors: Young Sik Kwon, Ansan-si (KR); Jae Heon Chung, Gwangmyeong-si (KR)

(73) Assignee: KOH YOUNG TECHNOLOGY INC., Seoul (KR)

( * ) Notice: Subject to any disclaimer, the term of this patent is extended or adjusted under 35 U.S.C. 154(b) by 166 days.

(21) Appl. No.: 15/386,205

(22) Filed: Dec. 21, 2016

(65) Prior Publication Data
US 2018/0049825 A1 Feb. 22, 2018

(30) Foreign Application Priority Data
Aug. 16, 2016 (KR) .................. 10-2016-0103716

(51) Int. Cl.
*A61B 34/30* (2016.01)
*A61B 34/20* (2016.01)
(Continued)

(52) U.S. Cl.
CPC .............. *A61B 34/30* (2016.02); *A61B 34/20* (2016.02); *A61B 90/14* (2016.02); *A61B 90/50* (2016.02);
(Continued)

(58) Field of Classification Search
CPC ......... A61B 90/14; A61B 90/50; A61B 90/11; A61B 2034/302; A61B 2034/304–306;
(Continued)

(56) References Cited

U.S. PATENT DOCUMENTS 5,257,998 A 11/1993 Ota et al.
5,269,305 A 12/1993 Corol
(Continued)

FOREIGN PATENT DOCUMENTS

EP 1 510 182 3/2005
EP 3 028 637 6/2016
(Continued)

OTHER PUBLICATIONS

Japanese Office Action with English translation dated Jun. 12, 2018 for Japanese Patent Application No. 2016-248816.

*Primary Examiner* — David C Eastwood
*Assistant Examiner* — Erich Herbermann
(74) *Attorney, Agent, or Firm* — Kile Park Reed & Houtteman PLLC

(57) ABSTRACT

A stereotactic surgery robot according to the present disclosure may include: a rotating unit that is configured to have a surgical instrument that is able to be attached thereto, and is configured to rotate the surgical instrument on at least one of two rotational axes according to an entry posture of the surgical instrument; a moving unit that is configured to move the rotating unit in the direction of at least one of three linear axes according to the position of a surgical target; and a surgical portion support unit that is configured to be connected to the moving unit, and is configured to be detachable with respect to an operating table, wherein the moving unit may move the rotating unit such that an intersection point of the two rotational axes matches the surgical target.

11 Claims, 13 Drawing Sheets

(51) Int. Cl.
  *A61B 90/50* (2016.01)
  *A61B 90/14* (2016.01)
  *A61B 90/10* (2016.01)
  *A61B 90/11* (2016.01)

(52) U.S. Cl.
  CPC ......... *A61B 90/11* (2016.02); *A61B 2034/302* (2016.02); *A61B 2090/103* (2016.02)

(58) Field of Classification Search
  CPC ......... A61B 34/20; A61B 34/30; A61B 34/37; A61B 2090/103; A61B 2090/508
  See application file for complete search history.

(56) References Cited

U.S. PATENT DOCUMENTS

| | | |
|---|---|---|
| 5,695,501 A | 12/1997 | Carol et al. |
| 2010/0026789 A1 | 2/2010 | Balogh |
| 2015/0025549 A1* | 1/2015 | Kilroy .................... A61B 90/60 606/130 |
| 2016/0220320 A1 | 8/2016 | Crawford et al. |
| 2017/0333143 A1 | 11/2017 | Yoshii |

FOREIGN PATENT DOCUMENTS

| | | |
|---|---|---|
| JP | 1991-106359 | 5/1991 |
| JP | 2008-513086 | 5/2008 |
| KR | 10-2010-0067846 | 6/2010 |
| WO | 01/97680 | 12/2001 |
| WO | 2006/033064 | 3/2006 |
| WO | 2010/068005 | 6/2010 |
| WO | 2013/192598 | 12/2013 |
| WO | 2014/151621 | 9/2014 |
| WO | 2016/125385 | 11/2016 |

* cited by examiner

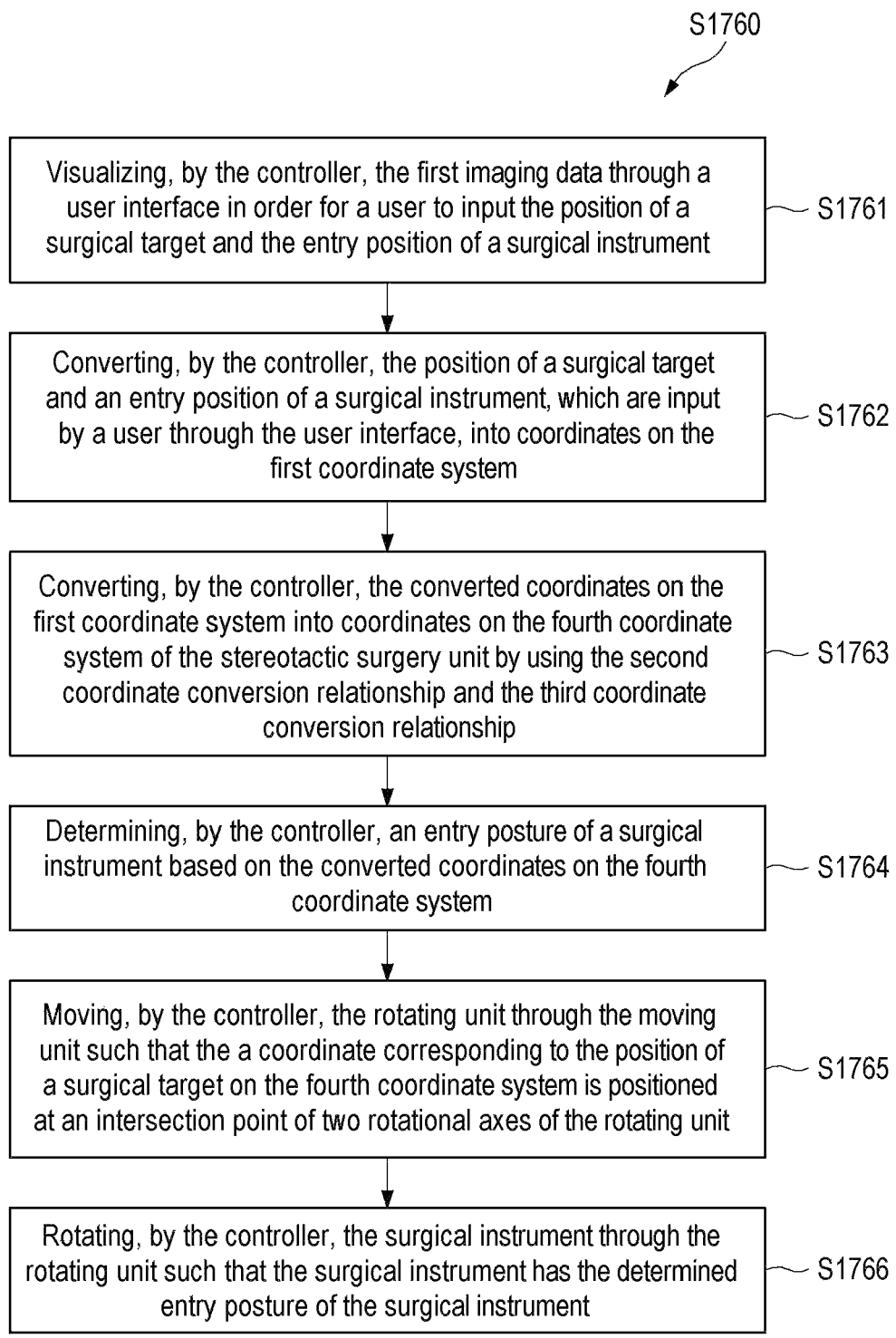

SURGICAL ROBOT FOR STEREOTACTIC SURGERY AND METHOD FOR CONTROLLING STEREOTACTIC SURGERY ROBOT

CROSS-REFERENCE TO RELATED APPLICATIONS

The present application claims priority from Korean Patent Application No. 10-2016-0103716 filed on Aug. 16, 2016, the entire subject matter of which is incorporated herein by reference.

TECHNICAL FIELD

The present disclosure relates to a surgical robot for stereotactic surgery, and further relates to a method for controlling the stereotactic surgery robot.

The present disclosure is derived from research conducted as a part of the Robot Industry Fusion Core Technology Development Project of the Ministry of Trade, Industry and Energy. [Project No. 10062800, Project Title: Development of Practical Technology of Medical Imaging based Brain Surgery Robot System through Clinical Trial]

BACKGROUND ART

Various stereotactic surgery instruments have been known. For example, Leksell Frame is used as a manual stereotactic surgery instrument for brain surgery. Leksell Frame has a structure in which a user is able to manually move the stereotactic surgery instrument along X, Y, and Z-axes and is able to rotate the same such that the position of the stereotactic surgery instrument corresponds to the position of an affected portion. However, in the case of using such a manual stereotactic surgery instrument, since the user should read gradations on the Leksell Frame with the naked eye to then determine and move the position of the surgery instrument, it tends to cause an error between the position of the affected portion and the surgery instrument.

Therefore, a technology for utilizing a robot for the stereotactic surgery has been introduced in order to improve the accuracy of positioning the surgical instrument. The stereotactic surgery robot is implemented with a robot arm that includes a driving arm assembly, wherein the robot arm is coupled to a fixed base and includes a plurality of arms that are connected in series. The position of the surgical instrument that is attached to the serial type of robot arm and the surgical accuracy thereof may be affected by all axes of the robot arm with a degree of freedom. That is, when an error occurs in the operation by using one axis of the robot arm, the error is added to another error that occurs in the operation by using another axis so that the errors caused by all axes are accumulated to then affect the surgical accuracy. In this case, when an operational error occurs at the driving end that is installed on the base, the error is added to other operational errors of a plurality of robot arms that are connected to the base so that the error is further amplified as it goes to the end of the robot arm. Therefore, in order to improve the surgical accuracy, it is preferable to set the distance between the base to which the robot arm is fixed and the affected portion to be short. However, if the distance between the base of the robot arm and the affected portion is shortened, the inertia of the robot arm becomes small. Therefore, an error tends to occur, and thus, it is difficult to make precise control of the robot arm. In addition, since a space between the base of the robot arm and the affected portion becomes small, the operating range of the robot arm may be reduced. In addition, in the case where the robot arm fixed to the base is disposed around the affected portion, there may be a risk that the user may collide with the robot arm when the user moves around the affected portion so that the movement of the user may be disrupted.

Meanwhile, the position of a surgical target and the entry position (or entry) of the surgical instrument should be specified for stereotactic surgery. In the case of brain surgery or nerve surgery, if the entry position of a surgical instrument is not properly set, the surgical instrument may come into contact with critical portions of the brain or nerves prior to approaching a surgical target in order to thereby put the patient in unnecessary danger. However, the conventional stereotactic surgery instrument is controlled in a state in which the movement of the surgical instrument according to the position of a surgical target is not independently separated from the movement of the surgical instrument according to the entry position of a surgical instrument. Therefore, if an error occurs between the actual position of the surgical instrument and the position of the surgical instrument, which is recognized by the stereotactic surgery robot system, the control of the surgical instrument for correcting the error may be complicated.

SUMMARY

The present disclosure provides a surgical robot for stereotactic surgery, which can improve the accuracy of stereotactic surgery and can secure the convenience of a surgical posture of the patient.

The present disclosure provides a method for controlling a stereotactic surgery robot, which can reduce a control error of the stereotactic surgery robot and can easily correct an error that has occurred.

The present disclosure provides a surgical robot for stereotactic surgery and a method for controlling a stereotactic surgery robot, which can reduce the complexity of the operation control of the surgical instrument by independently executing the operation control of the surgical instrument according to the position of a surgical target and the operation control of the surgical instrument according to the entry position of a surgical instrument.

The present disclosure provides a surgical robot system and a method for controlling a stereotactic surgery robot, which can easily control the stereotactic surgery robot based on the image of a surgical target, which is displayed on a user interface.

A stereotactic surgery robot according to an embodiment of the present disclosure includes: a rotating unit that is configured to have a surgical instrument that is able to be attached thereto, and is configured to rotate the surgical instrument on at least one of two rotational axes according to an entry posture of the surgical instrument; a moving unit that is configured to move the rotating unit in the direction of at least one of three linear axes according to the position of a surgical target; and a surgical portion support unit that is configured to be connected to the moving unit, and is configured to be detachable with respect to an operating table, wherein the moving unit may move the rotating unit such that an intersection point of the two rotational axes matches the surgical target.

According to an embodiment, the surgical portion support unit includes a connecting unit that is detachably connected to the moving unit.

According to an embodiment, the surgical portion support unit further includes: an angle adjusting unit that is configured to adjust the angle of the surgical portion; and a posture adjusting unit that is configured to include a height adjusting unit for adjusting the height of the surgical portion.

According to an embodiment, the surgical portion support unit further includes an operating table fixing unit that is configured to detachably fix a posture adjusting unit to the operating table while being connected to the posture adjusting unit.

According to an embodiment, the stereotactic surgery robot further includes a surgical portion fixing unit that is configured to be fixedly disposed in the surgical portion support unit and is configured to fix the surgical portion to prevent the movement of the surgical portion.

According to an embodiment, the surgical portion fixing unit includes a surgical portion fixing frame and a surgical portion fixing pin, and the surgical portion fixing frame is configured in a shape to prevent the surgical portion fixing frame from blocking a feature region when the imaging unit forms an image of the feature region of the surgical portion.

According to an embodiment, the stereotactic surgery robot further includes an insulating unit that is configured to be interposed between the surgical portion fixing frame and the surgical portion support unit.

According to an embodiment, the moving unit includes: a first direction driving unit configured to move along a first linear axial direction; a second direction driving unit configured to move along a second linear axial direction while being connected to the first direction driving unit; and a third direction driving unit configured to move along a third linear axial direction while being connected to the second direction driving unit, and wherein the rotating unit includes: a first rotational driving unit configured to rotate on the first rotational axis while one end of the first rotational driving unit is connected to the third direction driving unit; and a second rotational driving unit configured to rotate on the second rotational axis while one end of the second rotational driving unit is connected to the other end of the first rotational driving unit and while the surgical instrument is attached to the other end of the second rotational driving unit.

According to an embodiment, the first to third linear axial directions may be perpendicular to each other, and the first rotational axis and the second rotational axis may be perpendicular to each other.

According to an embodiment, a holder to which the surgical instrument is detachably attached may be attached to the other end of the second rotational driving unit.

According to an embodiment, a surgical instrument detecting unit for detecting the mounting of the surgical instrument may be further attached to the other end of the second rotational driving unit.

According to an embodiment, the third direction driving unit has a hole that is formed as being centered on the first rotational axis.

In a method of controlling a stereotactic surgery robot according to an embodiment of the present disclosure, the stereotactic surgery robot includes a rotating unit to which a surgical instrument is able to be attached and that rotates the surgical instrument about at least one of two rotational axes, a moving unit that moves the rotating unit, and a surgical portion support unit that is connected to the moving unit. In addition, the control method may include: receiving a position of a surgical target and an entry posture of the surgical instrument by the surgical robot; moving the rotating unit in the direction of at least one of three linear axes according to the position of the surgical target by the moving unit such that an intersection point of the two rotational axes matches the position of the surgical target; and rotating the surgical instrument on at least one of two rotational axes according to the entry posture of the surgical instrument by the rotating unit.

According to an embodiment, the stereotactic surgery robot may further include an angle adjusting unit that is configured to adjust the angle of the surgical portion and a height adjusting unit that is configured to adjust the height of the surgical portion, and the method may further include adjusting at least one of the angle or the height of the surgical portion by the angle adjusting unit and the height adjusting unit before determining the position of the surgical target and the entry posture of the surgical instrument.

According to an embodiment, the moving unit may include first to third direction driving units and the rotating unit may include first and second rotational driving units, wherein the moving of the rotating unit by the moving unit may include at least one of the following steps: moving the first direction driving unit along a first linear axial direction; moving the second direction driving unit along a second linear axial direction; and moving the third direction driving unit along a third linear axial direction, and wherein the rotating of the surgical instrument by the rotating unit may include at least one of the following steps: rotating the first rotational driving unit on the first rotational axis; and rotating the second rotational driving unit on the second rotational axis.

According to the surgical robot for stereotactic surgery and the method for controlling a stereotactic surgery robot of the present disclosure, the stereotactic surgery robot can be independently controlled according to the position of a surgical target and the entry position of a surgical instrument in order to thereby improve the surgical accuracy and in order to thereby simplify the control method. The surgical robot can be disposed close to the affected portion of the patient so that the patient's convenience and the operator's workability can be improved and so that a control error can be reduced.

In addition, according to the surgical robot system including the stereotactic surgery robot of the present disclosure, a surgeon can simply control the stereotactic surgery robot through a user interface, and even if the patient moves during the surgery, it is possible to reset a coordinate conversion relationship for controlling the surgical robot within a short time.

BRIEF DESCRIPTION OF THE DRAWINGS

The above and other features, and advantages of the present disclosure will be more apparent from the following detailed description taken in conjunction with the accompanying drawings, in which:

FIG. 19 is a flowchart showing a method for controlling a stereotactic surgery unit by using a coordinate conversion relationship for converting a coordinate from the coordinate system of imaging data representing a three-dimensional image that contains a surgical portion into the coordinate system of a stereotactic surgery unit, according to an embodiment of the present disclosure.

DETAILED DESCRIPTION

Figure 1:
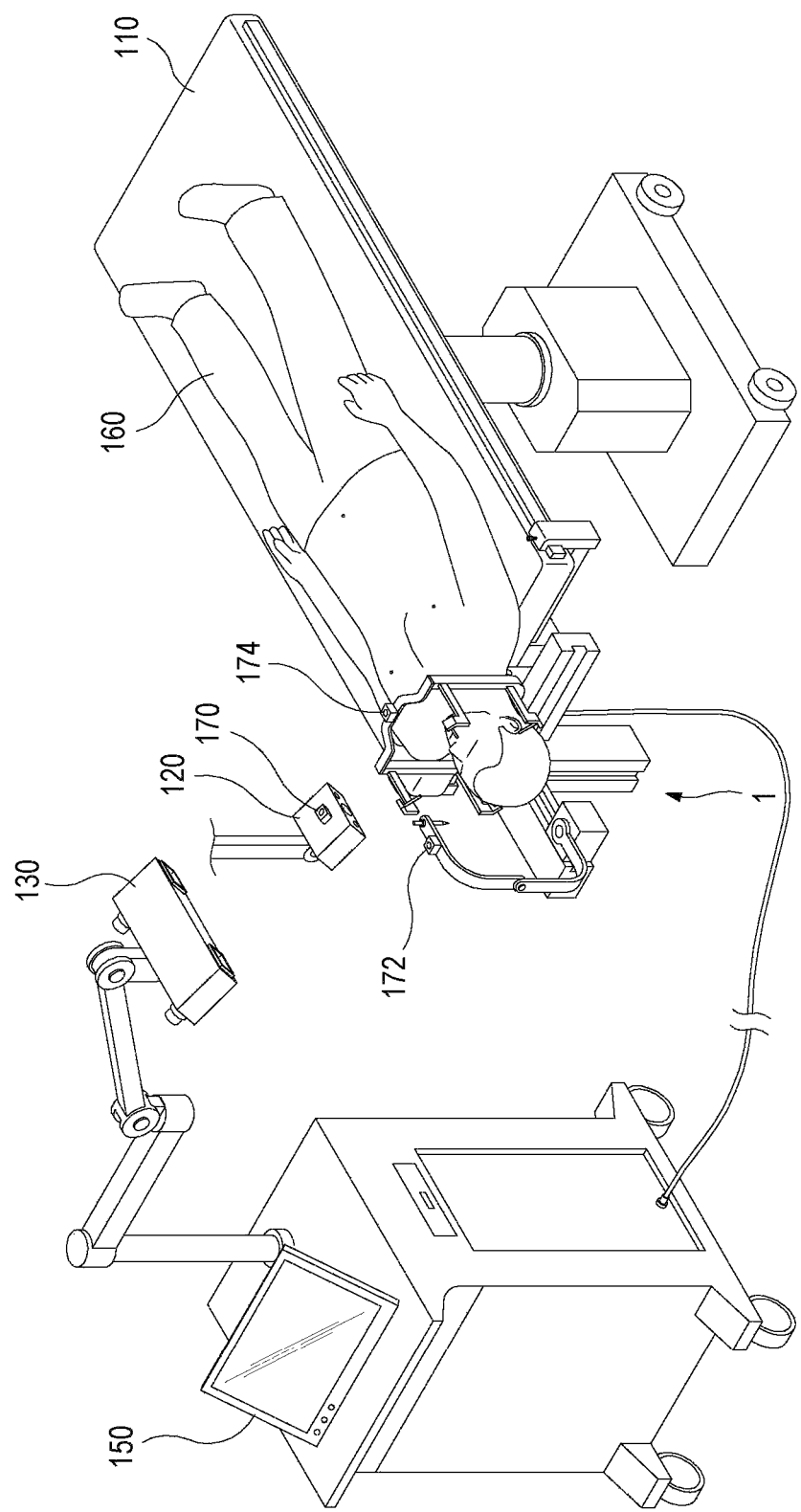
FIG. 1 is a view showing an example in which a surgical robot system is used for surgery, according to an embodiment of the present disclosure.

Embodiments of the present disclosure, which will be described below, are only examples that are illustrated for the purpose of explaining the present disclosure. The embodiments of the present disclosure may be conducted in various manners, and the present disclosure is not construed to be limited to the embodiments described below or to the detailed description of the embodiments.

The term "unit" that is used in the present embodiments refers to a software element and a hardware element, such as FPGA (field-programmable gate array) or ASIC (application specific integrated circuit). However, the "unit" is not limited to hardware and software. The "unit" may be configured to be in a storage medium that can be addressed, and may be configured to reproduce one or more processors. Accordingly, as an example, the "unit" includes elements, such as software elements, object-oriented software elements, class elements, or task elements, processors, functions, attributes, procedures, subroutines, program code segments, drivers, firmware, micro-codes, circuits, data, databases, data structures, tables, arrays, and variables. Functions that are provided in the elements and "unit" may be combined into fewer elements and "units," or may be further divided into additional elements and "units."

All the technical terms and scientific terms that are used in the present specification have the meanings that are commonly understood by those of ordinary skill in the art unless otherwise defined. All terms that are used in the present specification are selected for the purpose of describing embodiments of the present disclosure more clearly, and are not selected to limit the scope of the present disclosure.

The singular expressions that are described in the present specification may encompass plural expressions unless otherwise stated, and this will also be applied to the singular expressions shown in the claims.

The expressions, such as "first" or "second," which are used in various embodiments of the present disclosure, are used to separate a plurality of elements from each other, and are not intended to limit an order or importance of the corresponding elements.

The expressions, such as "include" or "have," which are used in the present specification, should be understood as open-ended terms that imply the possibility of including other embodiments unless particularly otherwise stated in the phrase or sentence that contains the corresponding expressions.

In the present specification, the expression "based on" will be used to describe one or more factors that affect the behavior or operation of the decision or determination that is described in the phrase that contains the corresponding expression, and does not exclude additional factors that affect the behavior or operation of the decision or determination.

In the present specification, the description that one element is "connected," or "coupled," to the other element should be understood that one element may be directly connected, or coupled, to the other element, and should be further understood that another new element may be interposed between one element and the other element.

Hereinafter, the embodiments of the present disclosure will be described in detail with reference to the accompanying drawings. The same reference numeral will be used for the same element throughout the drawings, and a duplicate description of the same element will be omitted.

<Stereotactic Surgery Robot System>

FIG. 1 shows an example in which a surgical robot system is used for surgery, which is able to perform stereotactic surgery, according to an embodiment of the present disclosure. As shown in the drawing, a surgeon (or a user) may proceed with stereotactic surgery for a patient 160 by using a surgical robot, such as a stereotactic surgery unit 1. The surgeon may check an image of a surgical portion, which is displayed in a user interface 150, and may determine the position of a surgical target where the surgery will be processed and the position through which a surgical instrument enters inside the patient 160.

If the surgeon inputs the position of a surgical target and the entry position of a surgical instrument through the user interface 150, the operation of the stereotactic surgery unit 1 may be controlled based on the same so that a surgical instrument that is attached to the stereotactic surgery unit 1 may approach the surgical target. Here, the "surgical target" may refer to a target (such as a tumor or a portion of an organ, a blood vessel, or a bone, which has a lesion) that is to be removed or treated by a surgical instrument. For example, the surgical target may be positioned inside the body of the patient 160 or on the external surface (or a skin) thereof. The "entry position" (or entry) of a surgical instrument may refer to the position on the external surface of the patient 160, with which the surgical instrument initially comes into contact or through which the surgical instrument passes in order to approach the surgical target in the case where the surgical target is positioned inside the patient's body. For example, in the case where the surgical instrument operates in order to eliminate a tumor that is positioned in the brain of the patient, the entry position of a surgical instrument may be set on the scalp of the patient.

According to an embodiment, the operation of the stereotactic surgery unit 1 may be accurately controlled by using an imaging unit 120 and a tracking unit 130 that are included in the surgical robot system. The imaging unit 120 may create imaging data that represents a three-dimensional external image of the surgical portion that includes a surgical target, such as a brain or a spine. Here, the "imaging data" may refer to data that is able to represent a photographed target, such as a surgical portion, in a form that can be visually recognized, and, for example, may include a two-dimensional or three-dimensional image that visually represents a surgical portion and coordinate system information that is related to the image. The tracking unit 130 may track markers 170, 172, and 174 that are attached to the imaging unit 120, the stereotactic surgery unit 1, and the patient 160 in order to thereby track the position and posture of each target that has the attached marker. According to the surgical robot system of the present disclosure, the current position of a surgical instrument may be determined, which is attached to the stereotactic surgery unit 1, by using the tracking unit 130. In addition, based on information that is created through the imaging unit 120 and the tracking unit 130, the surgical instrument may be moved from the current position to the position of a surgical target, which is input through the user interface 150.

According to an embodiment, the stereotactic surgery unit 1 may be used while being attached to the operating table 110. Therefore, even if the operating table 110 moves during the stereotactic surgery, the position through which the surgical instrument is guided to the surgical target may not vary because the stereotactic surgery unit 1 moves together with the operating table 110. In addition, if the stereotactic surgery unit 1 is used while being attached to the operating table 110, the stereotactic surgery unit 1 may be positioned near the patient. Thus, it is possible to precisely control a surgical instrument that is attached to the stereotactic surgery unit 1, and it is possible to prevent the movement of the surgeon from being interrupted by the stereotactic surgery unit 1.

Hereinafter, various embodiments of the surgical robot system of the present disclosure, which has been roughly described in the example of FIG. 1, will be described in more detail.

Figure 2:
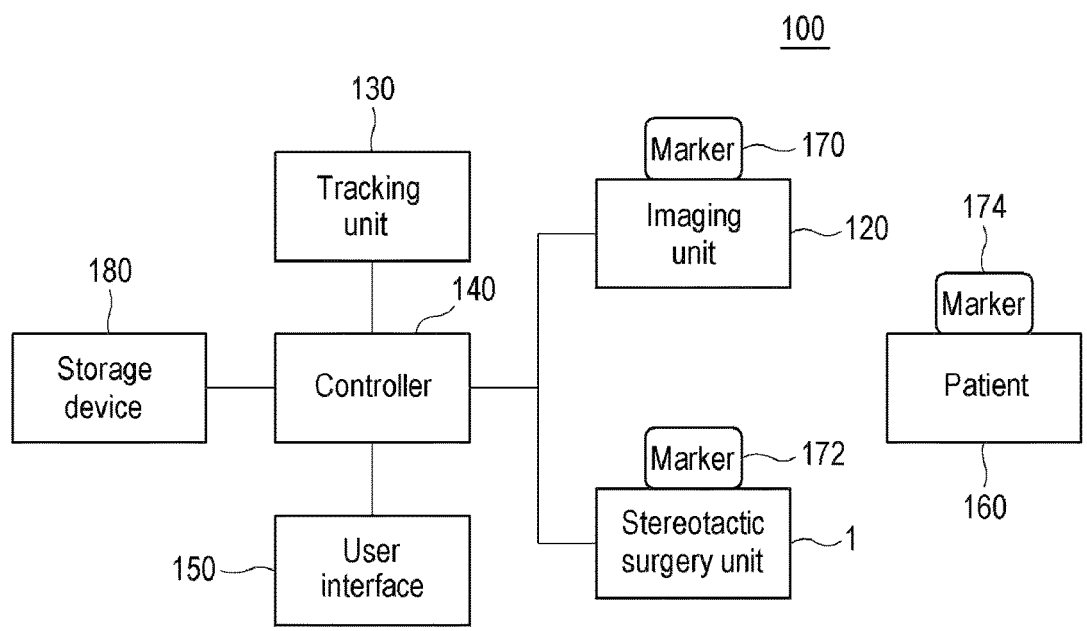
FIG. 2 is a block diagram showing a surgical robot system, according to an embodiment of the present disclosure.

FIG. 2 is a block diagram showing the surgical robot system 100, according to an embodiment of the present disclosure. The surgical robot system 100 may conduct stereotactic surgery, and may include an imaging unit 120, a tracking unit 130, and a controller 140. The stereotactic surgery unit 1 may include a surgical instrument that is able to conduct stereotactic surgery for a surgical target included in a surgical portion and a device that is able to guide the surgical instrument.

According to an embodiment, the stereotactic surgery unit 1 may be a stereotactic surgery robot that can operate with 5 degrees of freedom or more. For example, the stereotactic surgery unit 1 may move the surgical instrument in at least three axial directions, and may rotate the surgical instrument on at least two rotational axes. The stereotactic surgery unit 1 may be used while being attached to the operating table 110.

According to an embodiment, the stereotactic surgery unit 1 may independently perform the movement and the rotation of the surgical instrument according to the position of the surgical target and the entry position of the surgical instrument. Here, the configuration that the movement and the rotation of the surgical instrument are independently performed may mean that the configuration of moving the surgical instrument is implemented to be separated from the configuration of rotating the surgical instrument and the movement and the rotation of the surgical instrument may be individually controlled and performed according to the configuration. For example, the stereotactic surgery unit 1 may move the surgical instrument first according to the position of a surgical target, and may then determine the posture or direction of the approach or insertion of the surgical instrument to the surgical target according to the entry position of the surgical instrument. Thereafter, the stereotactic surgery unit 1 may rotate the surgical instrument such that the surgical instrument takes such a posture. Therefore, if the entry position of a surgical instrument is changed with respect to the same surgical target during the stereotactic surgery, the surgery may be resumed within a short time by simply changing only the posture of the surgical instrument. More detailed embodiments related to the configuration and operation of the stereotactic surgery unit 1 will be described later in the relevant portions of this disclosure.

The imaging unit 120 may create imaging data representing a two-dimensional or three-dimensional external image of the surgical portion. According to an embodiment, the imaging unit 120 may create imaging data that represents a surface image of the patient 160, or may create imaging data that represents an image of the surgical target or entry position of the surgical instrument (or the surrounding area of the entry position). According to an embodiment, the imaging unit 120 may create imaging data that represents a three-dimensional image based on the Phase Measuring Profilometry using a pattern light, etc.

The imaging data that is created by the imaging unit 120 may be transferred to the user interface 150 to then be visually displayed on the user interface 150. In addition, the imaging data that is created by the imaging unit 120 may be stored in a storage device 180 to then be used for the analysis of a surgery result or for the treatment after surgery.

According to an embodiment, the imaging data created by the imaging unit 120 may be registered with the imaging data representing a three-dimensional image of a surgical portion that includes a surgical target, which is previously photographed prior to surgery. The imaging data showing a three-dimensional image of a surgical portion may be stored in the storage device 180 prior to surgery. The user interface 150 may visually display a result of registering two pieces of imaging data. For example, the user interface 150 may be a display device that can display a two-dimensional or three-dimensional image that is represented by the data based on certain imaging data. The imaging data showing a three-dimensional image of a surgical portion, which is previously photographed prior to surgery, may be imaging data regarding a CT or MRI image of the surgical portion.

According to another embodiment, the controller 140 may control the stereotactic surgery unit 1 based on the imaging data that is created by using the imaging unit 120. More detailed embodiments related to the imaging unit 120 will be described later in the relevant part.

The tracking unit 130 is a device for tracking the movement of an object, and more specifically, is a device that is able to track the position and/or posture of an object. According to an embodiment, the tracking unit 130 may track a target to which a marker is attached by measuring the position and/or posture of the marker that is attached to the tracking target. For example, after attaching a marker to a surgical instrument, the tracking unit 130 may track the surgical instrument by tracking the position and/or posture of the marker that is attached to the surgical instrument.

According to an embodiment, the stereotactic surgery unit 1 may be controlled by using a result of tracking the markers 170, 172, and 174 that are attached to the imaging unit 120 and the stereotactic surgery unit 1, and are attached to, or near, the surgical portion of the patient 160, respectively. The markers may be attached to elements of the surgical robot system 100 or to various positions of the instruments/devices that are used for the stereotactic surgery according to the purpose of tracking. More detailed embodiments in relation to the configuration and operation of the tracking unit 130 will be described later in relevant portions of this disclosure.

The controller 140 may control the operation of various elements of the surgical robot system 100 that includes the stereotactic surgery unit 1, the imaging unit 120, the tracking unit 130, and the user interface 150. The controller 140 may store and execute control software for controlling the elements, which includes surgery planning software and navigation software. In addition, the controller 140 may include one or more processors, such as a CPU, that execute such software.

According to an embodiment, the controller 140 may be positioned in the operating room to then control the surgical robot system 100. According to another embodiment, the controller 140 may be positioned outside the operating room while being connected to the surgical robot system 100 through a wired or wireless network in order to thereby control the surgical robot system 100. According to another embodiment, the controller 140 may be implemented such that the functions thereof are distributed to each element of the surgical robot system 100. For example, a function of the controller 140 for controlling the tracking unit 130 may be implemented in the tracking unit 130, and a function of the controller 140 for controlling the imaging unit 120 may be implemented in the imaging unit 120. The controller 140 may be connected with a database that is installed inside or outside the operating room or hospital by a wired or wireless network, and may receive, from the database, a variety of data including the imaging data that is necessary for the surgery.

Hereinafter, the detailed embodiments of each elements included in the surgical robot system 100 will be described.

<Stereotactic Surgery Unit 1>

Figure 3:
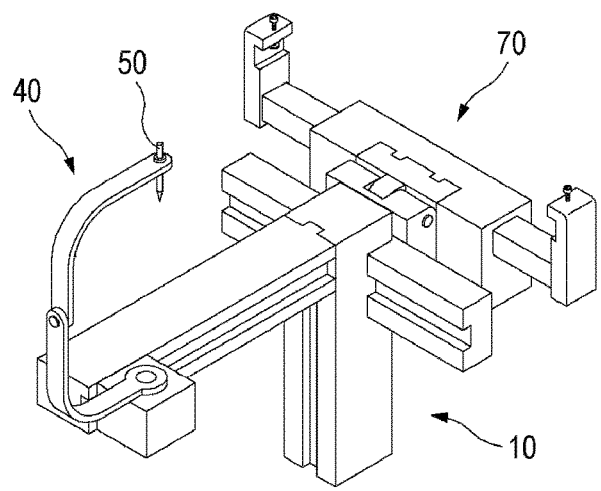
FIG. 3 is a perspective view showing a stereotactic surgery robot, according to an embodiment of the present disclosure.

FIG. 3 shows the stereotactic surgery robot 1 according to an embodiment of the present disclosure, which may be used as the stereotactic surgery unit 1 of FIG. 2. The stereotactic surgery robot 1 of the present embodiment may include a moving unit 10, a rotating unit 40, and a surgical portion support unit 70, and may be configured to be detachable with respect to the operating table. A surgical instrument 50 may be provided at one end of the rotating unit 40, and the stereotactic surgery robot 1 may control the moving unit 10 and the rotating unit 40 in order to thereby adjust the position and posture of the surgical instrument 50. The stereotactic surgery robot 1, according to the present embodiment, can move the moving unit 10 according to the position of a surgical target, and can rotate the rotating unit 40 according to the entry position or posture of a surgical instrument. The moving unit 10 and the rotating unit 40 may be independently controlled.

Figure 4:
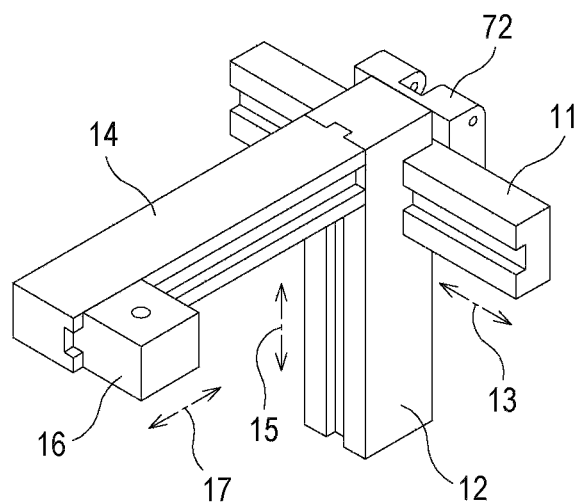
FIG. 4 is a perspective view of a moving unit, according to an embodiment of the present disclosure.

Hereinafter, the detailed configuration and operation of the moving unit 10 such that the rotating unit 40 is rotatably connected will be described with reference to FIGS. 4 and 5. According to an embodiment, the moving unit 10 may operate to allow the rotating unit 40 and the surgical instrument 50 that is fixed to one end of the rotating unit 40 to reciprocate in the direction of at least one of three axes, and thus, the moving unit 10 may have three degrees of freedom. The moving unit 10 may include a first to third direction driving units 12, 14, and 16 that move along the first to third linear axial directions 13, 15, and 17.

As an example in the present embodiment, the first to third linear axial directions 13, 15, and 17 are perpendicular to each other, and each driving unit 12, 14, or 16 may reciprocate along the perpendicular axes. According to another embodiment, the first to third linear axial directions 13, 15, and 17 may be arranged in a certain manner in which they are not perpendicular to each other. The first to third direction driving units 12, 14, and 16, for example, may be realized by using one of a variety of mechanical or electrical driving means that include a linear motor, a ball screw, or the like. In the present embodiment, the moving unit 10 may be detachably connected to a connecting unit 72 of the surgical portion support unit 70 through a fixing unit 11, and the rotating unit 40 may be rotatably connected to the third driving unit 16.

Figure 5:
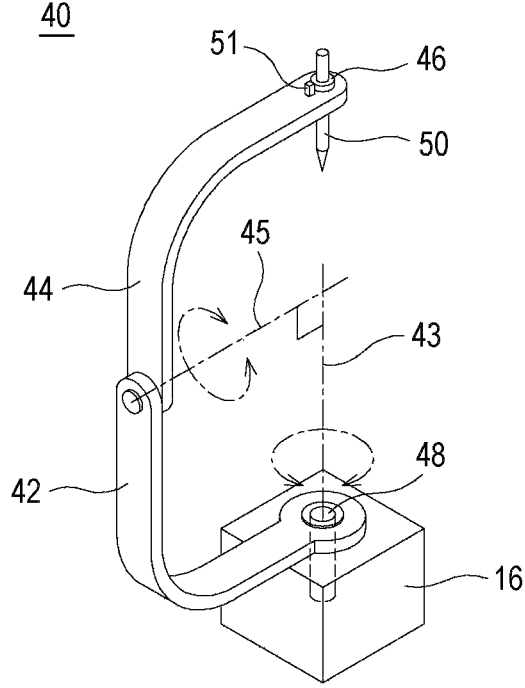
FIG. 5 is a perspective view of a rotating unit, according to an embodiment of the present disclosure.

Referring to FIG. 5, the detailed configuration and operation of the rotating unit 40 will be described. The rotating unit 40 may include a first rotational driving unit 42 that is coupled to the third direction driving unit 16 and a second rotational driving unit 44 that is coupled to the first rotational driving unit 42. The first and second rotational driving units 42 and 44 may rotate on the first and second rotational axes 43 and 45, respectively. For example, each of the first and second rotational driving units 42 and 44 may be realized by using one of various mechanical or electrical driving means that include a servo motor, a hydraulic motor, or the like.

As shown in the drawing, the first and second rotational driving units 42 and 44 may be designed in a circular arc shape or in a similar shape. The integral type of drape that can cover the entire rotating unit 40 may be mounted on the rotating unit 40 by adopting such a shape, and the drape may be sanitarily installed and replaced. The shapes of the first and second rotational driving units 42 and 44 are not limited to that of FIG. 5, and may be modified in a variety of shapes according to a surgical portion or surgery method in which the surgical robot system of the present disclosure is used.

The second rotational driving unit 44 of the present embodiment may include a surgical instrument 50 that is coupled to the second rotational driving unit 44 and a holder 46 that supports the surgical instrument 50 to be detachable. The holder 46 is configured to allow various types of surgical instruments to be easily attached to, or detached from, the same. By installing the holder 46 having such a configuration, the surgeon may perform a quick operation by shortening the replacement time of the surgical instrument.

Meanwhile, the second rotational driving unit 44 may further have a surgical instrument detecting unit 51 for sensing that the surgical instrument 50 has been attached or detached. When mounting of the surgical instrument 50 is detected by the surgical instrument detecting unit 51, the controller 140 may control the driving units 12, 14, and 16 of the moving unit 10 to be fixed without further moving. By the control of the operation of the moving unit 10 by the controller 140, it is possible to prevent a fatal medical accident that may be caused by the movement of the moving unit due to a malfunction of the surgical robot or physical impact during the operation, and a safe operation can be secured.

In the present embodiment, the first rotational axis 43 and the second rotational axis 45 may be configured to be perpendicular to each other, and the surgical instrument 50 may be maintained in a posture in which the front end thereof is directed to the intersection point of the first rotational axis 43 and the second rotational axis 45 by attaching the surgical instrument 50 to the second rotational driving unit 44. Therefore, even if the first rotational driving unit 42 and second rotational driving unit 44 rotate on the first rotational axis 43 and the second rotational axis 45, respectively, the intersection point of the first rotational axis 43 and the second rotational axis 45 may remain constantly in a posture in which the front end of the surgical instrument 50 is directed to the intersection point of the first rotational axis 43 and the second rotational axis 45 can be maintained. Since the front end of the surgical instrument 50 is maintained to be directed to the position of a surgical target while the rotating unit 40 is moved by the moving unit 10 such that the intersection point of the first rotational axis 43 and the second rotational axis 45 matches the position of the surgical target, the entry position of the surgical instrument 50 may be appropriately selected while the position of the surgical target remains constant. Therefore, even if the rotating unit 40 rotates the surgical instrument 50, the operation of the stereotactic surgery robot 1 may be controlled while maintaining the position of the surgical target to be constant. Here, the "position of a surgical target" may mean the position of a certain point of a surgical target or the position of a three-dimensional space that is occupied by the surgical target including that point. In addition, the "point" of a surgical target may mean a two-dimensional or three-dimensional region that is small enough to be visually recognized as a point, and it is not limited to a point in a mathematical or physical meaning.

Since the moving unit 10 having the configuration described above may move the rotating unit 40 according to the position of a surgical target, and the rotating unit 40 rotates the surgical instrument 50 according to the entry position of the surgical instrument, the moving unit 10 and the rotating unit 40 are independently controlled according to the position of a surgical target and the posture of a surgical instrument. Conventionally, a very complicated operation control method of the surgical robot was used in order to control the surgical instrument, and it was impossible to independently control according to the position of a surgical target and according to the entry position of the surgical instrument. However, according to the present embodiment, since the moving unit 10 and the rotating unit 40 can be independently controlled according to the position of a surgical target and the entry posture of a surgical instrument, the accuracy and efficiency of the control of the surgical robot and the surgical instrument may be improved.

In the present embodiment, a hole 48 may be further included, which is formed in the connecting portion of the first rotational driving unit 42 of the rotating unit 40 and the third direction driving unit 16, which is centered on the first rotational axis 43. An imaging device may be installed under the hole 48 in order to photograph medical images of a surgical portion or other affected portions. According to the configuration above, even when the position of a surgical instrument is calibrated, or even when a surgical portion is photographed in order to observe the condition of the patient during surgery, it is possible to prevent the photographed target from being blocked by the moving unit 10 or the rotating unit 40. In addition, the stereotactic surgery robot 1 may be operated along with the utilization of various medical imaging devices that include a C arm by forming the hole 48 in the direction of the first rotational axis 43 in the connecting portion of the first rotational driving unit 42 and the third direction driving unit 16 as described above. For example, the hole 48 may be realized by using a hollow rotary joint that is formed in the direction of the first rotational axis 43 in the connecting portion of the first rotational driving unit 42 and the third direction driving unit 16.

Figure 6:
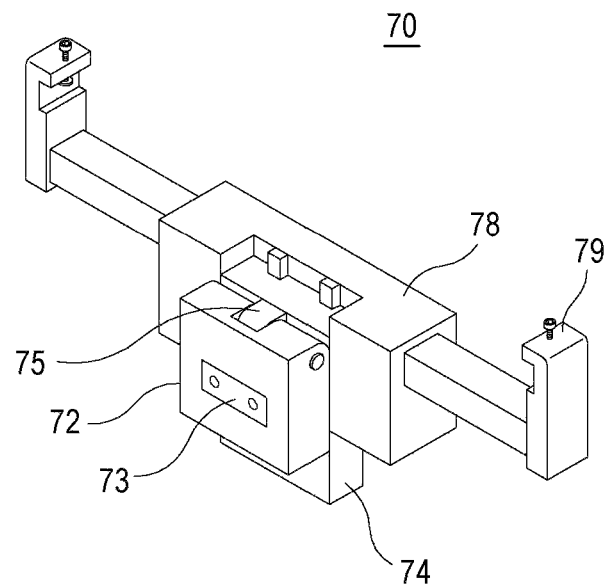
FIG. 6 is a perspective view of an operation portion support unit, according to an embodiment of the present disclosure.

The configuration and operation of the surgical portion support unit 70 will be described in more detail with reference to FIG. 6. The surgical portion support unit 70 may be provided in order to properly adjust the position of the moving unit 10 and the rotating unit 40 with respect to the patient or surgical portion. The surgical portion support unit 70 may allow the patient to take a more comfortable posture during surgery. In the present embodiment, the surgical portion support unit 70 includes a posture adjusting unit 74 and 75, a connecting unit 72, and an operating table fixing unit 78.

The connecting unit 72 may include a connecting member 73 that can be connected to the moving unit 10. The connecting member 73 may be realized by using bolts, nuts, or various mechanical connecting means including the same in order to connect the fixing unit 11 of the moving unit 10 and the connecting unit 72 detachably. The connecting member 73 may be realized by using a plurality of bolts and nuts, and it is possible to secure a reliable connection and fixing between the moving unit 10 and the surgical portion support unit 70 through the configuration above.

The posture adjusting unit 74 and 75 may include an angle adjusting unit 75 for adjusting the angle of a surgical portion and a height adjusting unit 74 for adjusting the height of a surgical portion. The angle adjusting unit 75 may be realized by using a manual or automatic mechanical device that can adjust the angle between the connecting unit 72 and the height adjusting unit 74 based on a single axis. The manual mechanical device may include various manual structures that include a hinge or a link structure, and the automatic mechanical device may include an actuator, such as a servo motor or a hydraulic cylinder. The height adjusting unit 74 may be coupled to the operating table fixing unit 78 to be movable in the vertical direction in order to thereby adjust the total height of the other elements that are connected to the height adjusting unit 74. The height adjusting unit 74 may be realized by using a manual or automatic mechanical device that includes a ball screw, a linear motor, or the like.

The operating table fixing unit 78 may be configured to secure the entire surgical portion support unit 70 to the operating table 110. Through this, the entire stereotactic surgery robot 1 including the moving unit 10 and the rotating unit 40 may be fixed to the operating table 110. The operating table fixing unit 78 may include a clamping unit 79 to solidly fix the operating table 110 and the operating table fixing unit 78. The clamping unit 79 may clamp the operating table fixing unit 78 to a portion (for example, a rail provided on the side) of the operating table 110 in order to thereby fix the entire surgical portion support unit 70 to the operating table 110. Although the operating table fixing unit 78 adopts the clamping unit 79 as an example in the present embodiment, the operating table fixing unit 78 may be fixed to the operating table 110 by using various fixing mechanisms, such as screws or tight-fit coupling.

Figure 7:
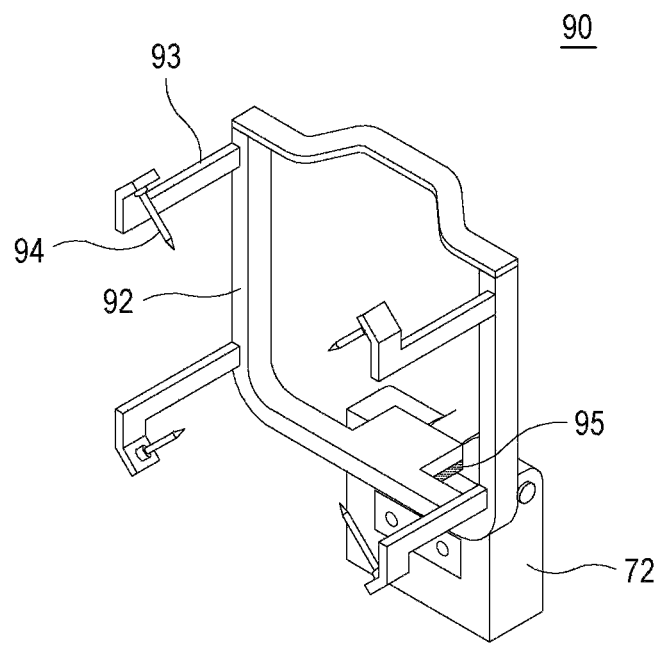
FIG. 7 is a perspective view of a patient fixing unit, according to an embodiment of the present disclosure.
Figure 8:
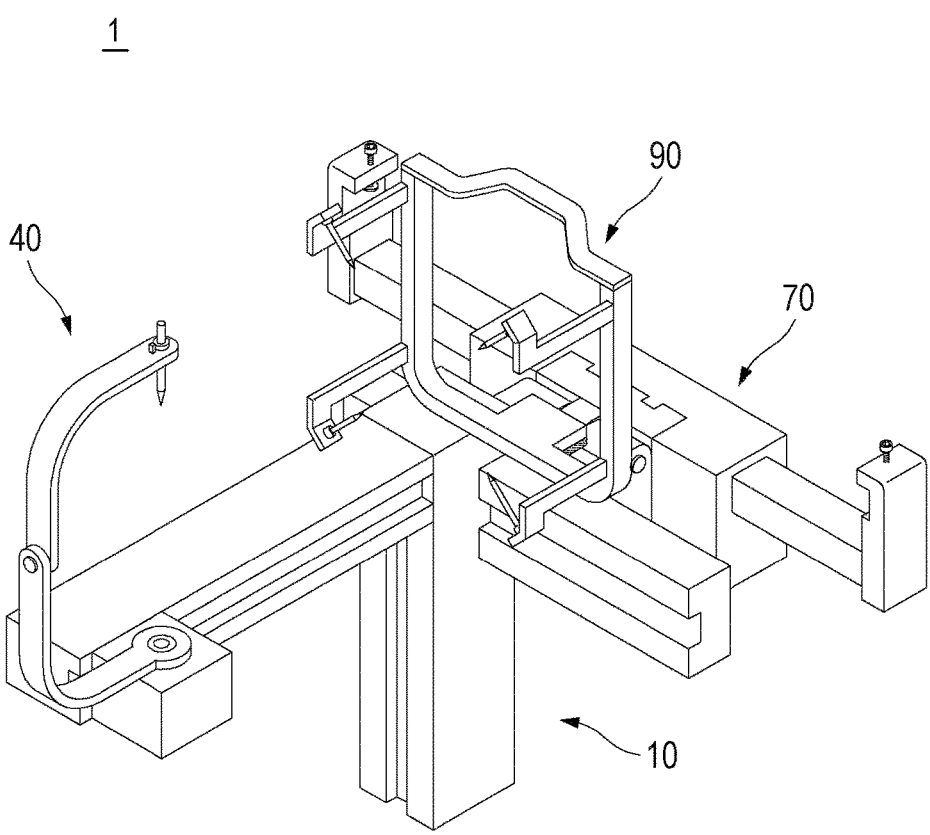
FIG. 8 is a perspective view of a stereotactic surgery robot to which a patient fixing unit is coupled, according to an embodiment of the present disclosure.

The detailed configuration and operation of the surgical portion fixing unit 90 will be described in more detail with reference to FIGS. 7 and 8. In general, the stereotactic surgery device is required to fix a surgical portion (for example, a patient's head) of the patient with respect to the surgical instrument without shaking. To this end, the surgical portion fixing unit 90 may include surgical portion fixing frames 92 and 93 and surgical portion fixing pins 94 in the present embodiment. The surgical portion fixing frames 92 and 93 are comprised of a lateral-direction surgical portion fixing frame 92 and a longitudinal-direction surgical portion fixing frame 93 for fixing a surgical portion, and a surgical portion fixing pin 94 is attached to one end of the longitudinal-direction surgical portion fixing frame 93, which is able to precisely fix the surgical portion of the patient. Although the present embodiment shows an example in which the surgical portion fixing unit 90 includes a single lateral-direction surgical portion fixing frame 92 and four longitudinal-direction surgical portion fixing frames 93, the number of lateral-direction surgical portion fixing frames 92 or longitudinal-direction surgical portion fixing frames 93 and the connecting configuration therebetween may be properly modified as necessary.

The surgical portion fixing frames 92 and 93 of the present embodiment may be modified in an appropriate form in order to improve the compatibility of usage with the imaging unit 120. For example, in the case of surgery for the patient's head, an image of the patient is photographed, and then feature regions, such as eyes, a nose, a glabella, or ears of the patient, are extracted from the image. Thus, it is possible to predict and determine the precise position of a surgical portion (that is, the head) of the patient. In this case, the surgical portion fixing frames 92 and 93 may be configured so as not to interrupt the imaging of a specific region of the patient. In the present embodiment, for example, the upper central portion of the lateral-direction surgical portion fixing frame 92 may have a concave shape so as not to interfere with a nose portion of the patient, and the longitudinal-direction surgical portion fixing frame 93 may be coupled to the outermost of the lateral-direction surgical portion fixing frame 92 so as not to cover the ear portion of the patient. Therefore, the lateral-direction surgical portion fixing frame 92 and the longitudinal-direction surgical portion fixing frame 93 may be prevented from blocking the feature regions of the patient in order to thereby ensure the imaging of the feature regions of the patient by the imaging unit 120 during surgery.

The surgical portion fixing frames 92 and 93 and the surgical portion fixing pins 94, for example, may be made of a material, such as a metal, that has durability and rigid characteristics. However, in the case of using such a metal material, the metal material may come into contact with an electric device, such as electronic control equipment or measuring equipment, to then cause an electric shock to the patient. Thus, in order to prevent this, insulating means may be connected to the surgical portion fixing frames 92 and 93 to prevent electric contact between the electric device and the patient. More specifically, the surgical portion fixing frames 92 and 93 and the connecting unit 72 may be connected to be insulated from each other by interposing the insulating means 95 between the surgical portion fixing frames 92 and 93 and the connecting unit 72.

Since the surgical portion fixing unit 90 may be detachably connected to the connecting unit 72 in the present embodiment, the surgical portion fixing unit 90 may be selected, which has a shape and size to conform to the purpose of the surgery, and may be simply replaced. In addition, since the surgical portion fixing unit 90 may be directly fixed to the surgical portion support unit 70, the surgical portion fixing unit 90 may stably fix the surgical portion even in the case of the movement of the moving unit 10 and the rotation of the rotating unit 40.

The stereotactic surgery robot 1 of the present embodiment may be automatically controlled through the controller 140. Hereinafter, the control method of the stereotactic surgery robot 1 will be described in more detail.

The controller 140 may determine the position of a surgical target and the entry position of a surgical instrument according to a surgery plan, and may output a control signal to allow the moving unit 10 and the rotating unit 40 to move the surgical instrument according to the determined positions. Based on the control signal output from the controller 140, the moving unit 10 may move in the direction of at least one of three axes according to the position information of a surgical target such that the intersection point of two rotational axes matches the position of a surgical target. In addition, based on the control signal output from the controller 140, the rotating unit 40 may rotate the surgical instrument 50 on at least one of two rotational axes according to entry posture information of the surgical instrument. More specifically, based on the control signal output from the controller 140, the moving unit 10 may move: the first direction driving unit along the first linear axial direction; the second direction driving unit along the second linear axial direction; or the third direction driving unit along the third linear axial direction. In addition, the rotating unit 40 may rotate the first rotational driving unit on the first rotational axis, or may rotate the second rotational driving unit on the second rotational axis based on the control signal of the controller 140.

As described above, since the moving unit 10 and the rotating unit 40 are independently controlled according to the position of a surgical target and the entry posture of a surgical instrument, it is possible to reduce an error in controlling the operation of the surgical robot 1, and even if an error occurs, additional operation control that is necessary to correct the error may be simplified.

In addition, the controller 140 may control the angle adjusting unit 75 and the height adjusting unit 74 to adjust at least one of the angle or height of the surgical portion.

Although the stereotactic surgery robot 1, according to the present disclosure, has been described through the exemplary embodiment, the embodiment may be comprehensively applied to various surgical portions (a head, a spine, or joints of the body) to which the stereotactic surgery can be applied.

<Tracking Unit 130>

The tracking unit 130 is a device that is able to track the movement of an object, and more specifically, is a device that is able to measure the position and/or posture of an object. Although a tracking method is not particularly limited, in general, an optical tracking method based on optical technology or an electromagnetic tracking method based on electromagnetic technology may be used. In addition, various tracking methods may be used in combination.

The position measured by the tracking unit 130, for example, may be defined as spatial coordinates, such as coordinates on the X, Y, and Z axes of an orthogonal coordinate system. The posture measured by the tracking unit 130 may be defined as rotation information, such as roll, pitch, or yaw. 6 degrees of freedom of the position and posture of an object, which are defined as described above, may be measured for an accurate tracking of an object.

According to an embodiment, the tracking unit 130 may measure the position and/or posture of the marker that is attached to an object in order to thereby track the object. For example, after attaching a marker to a surgical instrument, the tracking unit 130 may measure the position and/or posture of the marker attached to the surgical instrument in order to thereby track the surgical instrument.

According to an embodiment, the tracking unit 130 may measure the position of a marker by using a retroreflector as a marker. According to another embodiment, a structure that has three or more markers attached thereto may be attached to a tracking target in order to simultaneously measure the position and posture of the tracking target. In this case, the retroreflector may be used as a marker, and any type of marker may be used if the tracking unit 130 can recognize the position of the marker. According to an embodiment, the position and posture of the tracking target may be simultaneously measured by comparing a geometric position relationship between three or more markers that are measured through the tracking unit 130 with a geometric position relationship between three or more markers, which is pre-stored.

Figure 9:
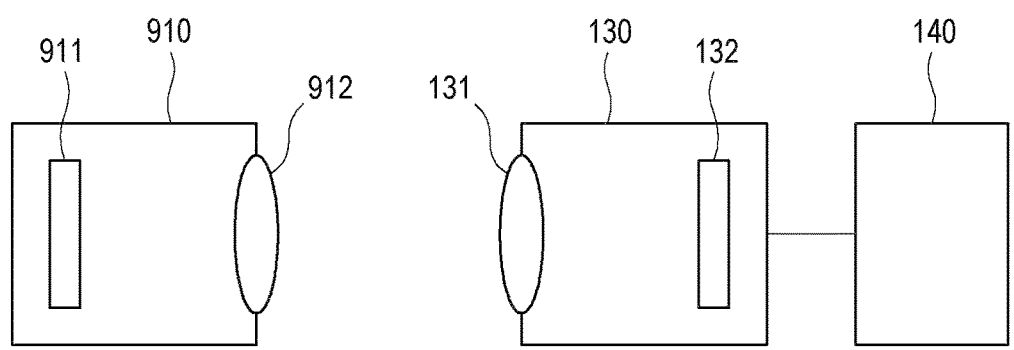
FIG. 9 is a block diagram showing a marker and a tracking unit to explain the operation of the tracking unit, according to an embodiment of the present disclosure.

Meanwhile, the position and posture of an object to which a marker is attached may be measured by using a single marker in order to simplify the marker. FIG. 9 is a block diagram showing a marker 910 and a tracking unit 130 that may be used in an optical tracking method using a single marker, according to an embodiment of the disclosure. The marker 910 may include one or more pattern parts 911 where a pattern is formed and a first lens 912 that is able to enlarge and transmit the pattern of the pattern part 911. The tracking unit 130 may include a second lens 131 and an image-forming device 132 that can form an image of the pattern of the pattern part 911, which is transmitted from the marker 910. According to an embodiment, in order to increase a recognition range of the pattern of the pattern part 911 or in order to increase a recognition rate of the pattern thereof, two or more tracking units 130 may be used, and two or more image-forming devices 132 may be included in a single tracking unit 130.

The pattern that is formed in the pattern part 911 may provide information to measure the position and posture of the marker 910. According to an embodiment, a plurality of patterns may be formed on the pattern part 911 to be arranged in a regular shape and spacing, and the position and posture of the marker 910 may be determined by using the image on which the pattern is formed.

According to an embodiment, when the image-forming device 132 forms an image with all or some of the pattern that is implemented in the pattern part 911, the controller 140 may extract a change in the size of a region where the pattern is viewed in the formed image, and may determine the position of the marker 910 based on the same. More specifically, when the position of the marker 910 varies, the size of the image-formed pattern varies as well. Such a size change of the pattern may be calculated as a position by comparing the diameter and the focal length of the lens 131.

According to another embodiment, the controller 140 may calculate the position of the marker 910 by using triangulation based on the fact that the positions of regions where all or some of the pattern is viewed are different in the images that are formed in two image-forming devices, respectively. According to an embodiment, the controller 140 may determine the position of the marker 910 based on a change in the position of each pattern region in the pattern. According to an embodiment, a function of the controller 140 for controlling the tracking unit 130 may be integrated with the tracking unit 130.

The marker 910 may be implemented as an active marker or as a passive marker. In the case of an active marker, the marker 910 may include a light source therein. Thus, the light source in the marker 910 may emit a light onto the pattern part 911, and the emitted light may pass through the pattern formed on the pattern part 911, or may be reflected from the pattern. The tracking unit 130 may receive the light passing through, or reflected from, the pattern, and may form an image of the pattern of the pattern part 911. The controller 140 may track the position and posture of the marker 910 based on the image that is formed as described above.

In the case of a passive marker, a light source for emitting a light onto the marker 910 may be disposed on the outside of the marker 910. Therefore, the light source located outside of the marker 910 may emit a light onto the marker 910, and the emitted light may pass through the pattern formed on the pattern part 911, or may be reflected from the pattern. The tracking unit 130 may receive the light passing through, or reflected from, the pattern, and may form an image of the pattern of the pattern part 911. The controller 140 may track the position and posture of the marker 910 based on the image that is formed as described above. If the surgery place is bright enough for the pattern of the marker 910 to be clearly recognized by the tracking unit 130, the marker 910 may be tracked without additional light sources.

According to an embodiment, the marker 910 may be implemented such that the focus of the first lens 912 is on a pattern plane of the pattern part 911. To this end, the shape of the pattern plane of the pattern part 911 may be implemented to match the shape of a plane on which the focus of the first lens 912 is, or the first lens 912 may be designed such that the focus of the first lens 912 is on the pattern plane of the pattern part 911.

If the marker 910 is implemented such that the focus of the first lens 912 is on the pattern plane of the pattern part 911, and if the image-forming device 132 of the tracking unit 130 is positioned in the focal length of the second lens 131, the optical system of the marker 910 and the tracking unit 130 may form an infinity optical system. If the marker 910 and the tracking unit 130 form an infinity optical system, the tracking unit 130 may form an enlarged pattern image through the infinity optical system. Thus, even if the marker 910 is far away from the tracking unit 130, a recognition rate of the pattern in the tracking unit 130 may be improved.

The tracking unit 130 may form an image of the pattern transmitted through the second lens 131 by using the image-forming device 132. The image-forming device 132 is a device for converting image information that is transmitted through a light into an electric signal, and typically, it may be implemented by using a CMOS image sensor, a CCD, or the like. According to an embodiment, the image-forming device 132 may form an image at the position corresponding to the focal length of the second lens 131.

<Imaging Unit 120>

The imaging unit 120 is a device that is able to create imaging data that represents an external image of a surgical portion. According to an embodiment, the imaging unit 120 may obtain a surface image of the patient 160, or may create imaging data representing an image of a surgical portion or the entry position of a surgical instrument (or the surrounding area of the entry position). Although the imaging unit 120 may be a device that can create imaging data representing two-dimensional images, such as general camera images, it may be a device that can create imaging data representing three-dimensional images that is necessary for the process of a precise surgery, such as stereotactic surgery.

According to an embodiment, the imaging unit 120 may create imaging data that represents three-dimensional images based on a Phase Measuring Profilometry by using a pattern light or the like. For example, imaging data representing three-dimensional images may be created by processing images that are photographed by irradiating a pattern light in a regular form onto the patient. Although the pattern light may have the intensity of illumination in a sine wave form, such as a lattice pattern light, it is not limited thereto. The irradiated pattern light may vary in the intensity of light on the surface of the patient 160 depending on the curvature of the surface of the patient 160, and imaging data representing three dimensional images may be created by creating phase data from the same and by calculating the height of each of the points that constitute the surface.

According to an embodiment, the imaging unit 120 may create imaging data representing three-dimensional images by an image processing unit that is included in the imaging unit 120. According to another embodiment, the controller 140 may receive the image data that is obtained by the imaging unit 120, and may then process the image data in order to thereby create imaging data representing three-dimensional images.

Figure 10:
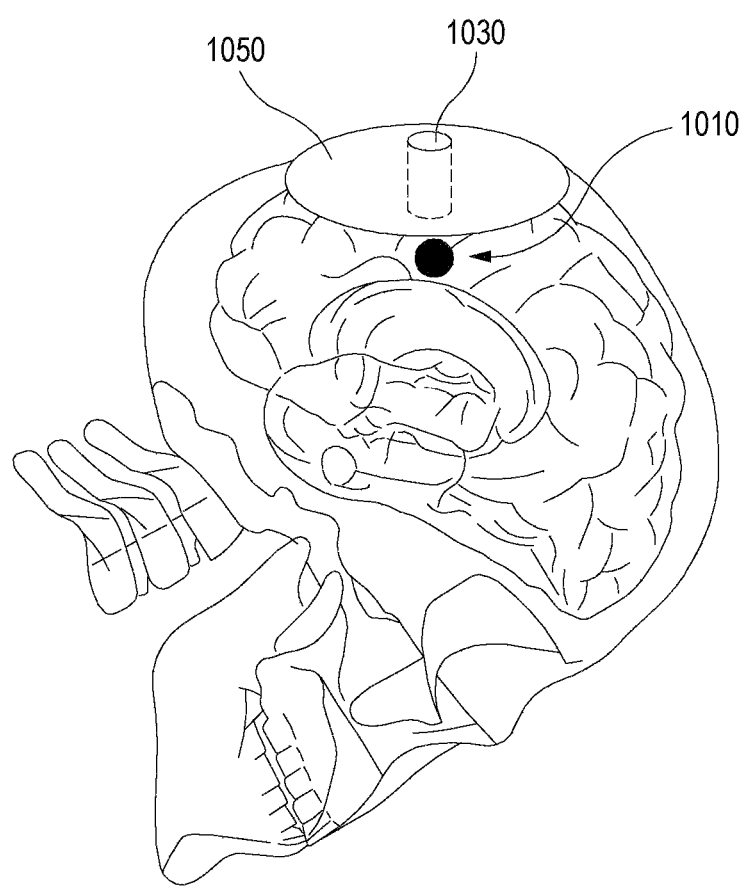
FIG. 10 is a view showing a result of the image registration between an image around the entry position of a surgical instrument, which is obtained through a imaging unit, and an image of a patient, which contains a surgical portion that is photographed prior to surgery, according to an embodiment of the present disclosure.

According to an embodiment, the imaging data created by the imaging unit 120 may be visually displayed through the user interface 150. According to another embodiment, two images may overlap each other by using an image registration between an imaging unit image that is represented by the imaging data that is created by the imaging unit 120 and the other image, and the result thereof may be visually displayed through the user interface 150. For example, as shown in FIG. 10, an imaging unit image may overlap a surgical portion image by using an image registration between the imaging unit image for a surrounding area 1050 of the entry position 1030 of the surgical instrument, which is obtained by using the imaging unit 120, and a surgical portion image including a surgical target 1010, which is obtained prior to surgery.

According to an embodiment, the image registration may be conducted by using the imaging unit image and at least a portion of a surgical portion that is commonly included in the other image to be registered with the same. According to another embodiment, an imaging unit image and the other image to be registered with the same are obtained so as to include the same fiducial marker, and thereafter, the image registration may be performed by using the fiducial marker that is included in the two images.

<Method of Controlling Surgical Robot System 100>

In general, stereotactic surgery is intended for a portion, such as a brain, that is hardly able to be identified by the surgeon with the naked eye. Therefore, the surgeon may determine a surgical target by analyzing a three-dimensional image, such as a CT or MRI image, of the surgical portion including a surgical target in the body of the patient 160 or by analyzing a two-dimensional sectional image of the three-dimensional image, and may determine the position in which the surgical instrument safely enters the surgical target. For example, when the CT image is displayed through the user interface 150, the surgeon may determine the position of a surgical target and/or the entry position of a surgical instrument by checking the CT image, and may input the determined positions through the user interface 150. The stereotactic surgery unit 1 of the present invention may be controlled based on the position of a surgical target and/or the entry position of a surgical instrument, which are input by the surgeon.

Figure 11:
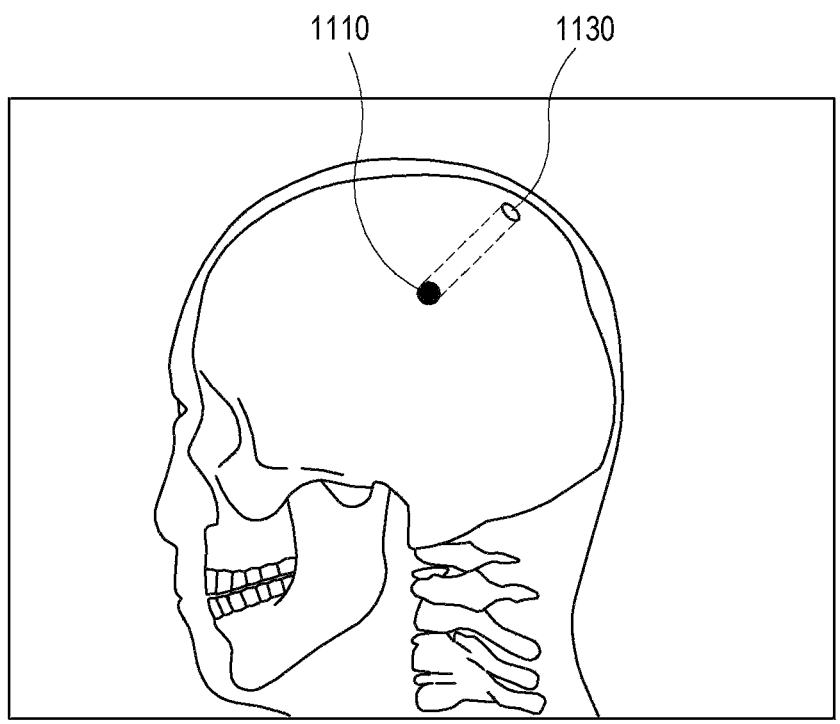
FIG. 11 is a view in which the position of a surgical target and the entry position of a surgical instrument are displayed on the three-dimensional image of the patient, which contains a surgical portion that is photographed prior to surgery, according to an embodiment of the present disclosure.

FIG. 11 shows a result in which a surgeon inputs the position 1110 of a surgical target and the entry position 1130 of a surgical instrument into a three-dimensional image of a surgical portion. According to an embodiment, the user, such as a surgeon, may input, by using a touch screen or the like, the position 1110 of a surgical target or the entry position 1130 of a surgical instrument into an image that is displayed through the user interface 150. According to another embodiment, the user may input the position 1110 of a surgical target or the entry position 1130 of a surgical instrument by typing the coordinate values.

When the position 1110 of a surgical target or the entry position 1130 of a surgical instrument is input through the user interface as described above, the controller 140 may control the operation of the stereotactic surgery unit 1 based on the input position 1110 of the surgical target.

According to an embodiment, the controller 140 may move the moving unit 10 of the stereotactic surgery unit 1 in a direction of at least one of three axes based on the input position 1110 of a surgical target. The rotating unit 40 for rotating the surgical instrument may be attached to the moving unit 10. Therefore, the rotating unit 40 may be moved with the movement of the moving unit 10. According to an embodiment, the controller 140 may move the rotating unit through the moving unit 10 such that the coordinate corresponding to the position of a surgical target is positioned at the intersection point of two rotational axes of the rotating unit 40.

According to an embodiment, the controller 140 may determine the entry posture of a surgical instrument based on the position 1110 of a surgical target and the entry position 1130 of a surgical instrument, which are input by the user. The controller 140 may rotate the rotating unit 40 to which the surgical instrument is attached on at least one of two rotational axes such that the surgical instrument has the determined entry posture of the surgical instrument.

The stereotactic surgery unit 1 may be driven based on the coordinate system of the stereotactic surgery unit 1. However, the position 1110 of a surgical target and the entry position 1130 of a surgical instrument, which are input through the user interface 150, are on the coordinate system of the image that is displayed on the user interface 150 rather than the coordinate system of the stereotactic surgery unit 1. Accordingly, in order to control the stereotactic surgery unit 1 based on the coordinate system of the stereotactic surgery unit 1, the position 1110 of a surgical target and the entry position 1130 of a surgical instrument, which are input based on the coordinate system of the image displayed on the user interface 150, should be converted into the positions based on the coordinate system of the stereotactic surgery unit 1.

According to an embodiment, the controller 140 may receive imaging data ("the first imaging data") that represents a three-dimensional image, such as a CT or MRI image, which is previously photographed prior to surgery. The first imaging data may be imaging data related to a surgical portion that includes a surgical target. The first imaging data may be pre-stored in the storage device 180 prior to surgery. The controller 140 may receive imaging data ("the second imaging data") that represents a three-dimensional external image of the surgical portion, which is created through the imaging unit 120. The controller 140 may: (i) create the first coordinate conversion relationship for converting a coordinate from the first coordinate system of the first imaging data into the second coordinate system of the second imaging data; and (ii) track the position and posture of the imaging unit 120 by using the tracking unit 130.

The controller 140 may create a coordinate conversion relationship for converting a coordinate from the first coordinate system of the first imaging data into the fourth coordinate system of the stereotactic surgery unit 1 by using the first coordinate conversion relationship and the position and posture of the imaging unit 120.

Hereinafter, a more detailed description will be made with reference to FIG. 12. First, the user may input the position 1110 of a surgical target and the entry position 1130 of a surgical instrument through the user interface 150. The controller 140 may convert the position 1110 of a surgical target and the entry position 1130 of a surgical instrument, which are input by the user, into the coordinates on the first coordinate system 1210 of the first imaging data.

According to an embodiment, in order to convert the position on the first coordinate system 1210 of the first imaging data into the position on the fourth coordinate system 1230 of the stereotactic surgery unit 1, the coordinate on the first coordinate system 1210 of the first imaging data may be converted in sequence into the coordinate on the third coordinate system 1220 of the patient marker 174, and then into the coordinate on the fourth coordinate system 1230 of the stereotactic surgery unit 1. For such coordinate conversion, it is possible to obtain (i) the second coordinate conversion relationship for converting the coordinate from the first coordinate system 1210 of the first imaging data into the third coordinate system 1220 of the patient marker 174 and (ii) the third coordinate conversion relationship for converting the coordinate from the third coordinate system 1220 of the patient marker 174 into the fourth coordinate system 1230 of the stereotactic surgery unit 1. Here, the patient marker 174 may be a marker that is attached to a surgical portion of the patient 160, or may be a marker that is attached to a target, such as the surgical portion fixing unit 90 of the stereotactic surgery unit 1, that is disposed close to a surgical portion and can be moved integrally with the patient 160. One or more patient markers 174 may be attached to the target.

Figure 13:
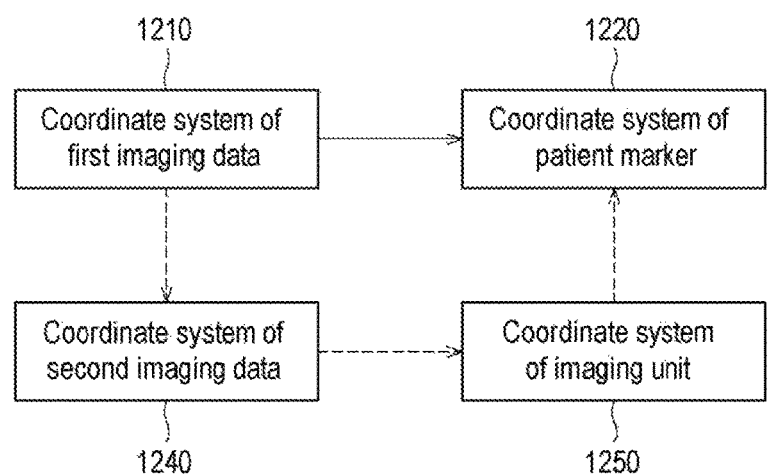
FIG. 13 is a view to explain a method for converting a coordinate from the coordinate system of imaging data representing a three-dimensional image that contains a surgical portion into the coordinate system of a patient marker, according to an embodiment of the present disclosure.

The second coordinate conversion relationship for converting the coordinate from the first coordinate system 1210 of the first imaging data into the third coordinate system 1220 of the patient marker 174 may be obtained by using (i) the first coordinate conversion relationship for converting the coordinate from the first coordinate system 1210 of the first imaging data into the second coordinate system 1240 of the second imaging data and (ii) the position and posture of the imaging unit 120, which are obtained by using the tracking unit 130. More specifically, as shown in FIG. 13, when the coordinate on the first coordinate system 1210 of the first imaging data may be converted in sequence into: the coordinate on the second coordinate system 1240 of the second imaging data; the coordinate on the fifth coordinate system 1250 of the imaging unit 120; and then the coordinate on the third coordinate system 1220 of the patient marker 174, the coordinate may be converted from the first coordinate system 1210 of the first imaging data into the third coordinate system 1220 of the patient marker 174.

The second imaging data may be created by using the imaging unit 120 prior to the process of stereotactic surgery or in the process of stereotactic surgery. According to an embodiment, the first coordinate conversion relationship for converting the coordinate from the first coordinate system 1210 of the first imaging data into the second coordinate system 1240 of the second imaging data may be created by using an image registration between a three-dimensional image represented by the first imaging data and a three-dimensional image represented by the second imaging data. The image registration between a three-dimensional image represented by the first imaging data and a three-dimensional image represented by the second imaging data may be performed by using at least some of the surgical portion that is commonly included in both the images. According to another embodiment, after obtaining the first imaging data and the second imaging data that include data related to the same fiducial marker, the image registration may be performed by using the fiducial marker. Furthermore, other various known image registration methods may be used to create the first coordinate conversion relationship.

According to an embodiment, the fourth coordinate conversion relationship for converting the coordinate from the second coordinate system 1240 of the second imaging data into the fifth coordinate system 1250 of the imaging unit 120 may be created by using (i) the coordinate conversion relationship for converting the coordinate from the reference coordinate system of the optical system of the imaging unit 120 into the fifth coordinate system 1250 of the imaging unit 120 and (ii) the coordinate conversion relationship for converting the coordinate from the second coordinate system 1240 of the second imaging data into the reference coordinate system of the optical system of the imaging unit 120.

The fifth coordinate conversion relationship for converting the coordinate from the fifth coordinate system 1250 of the imaging unit 120 into the third coordinate system 1220 of the patient marker 174 may be created by using (i) the coordinate conversion relationship for converting the coordinate from the fifth coordinate system 1250 of the imaging unit 120 into the coordinate system of the tracking unit 130 and (ii) the coordinate conversion relationship for converting the coordinate from the third coordinate system 1220 of the patient marker 174 into the coordinate system of the tracking unit 130.

At this time, the coordinate conversion relationship for converting the coordinate from the fifth coordinate system 1250 of the imaging unit 120 into the coordinate system of the tracking unit 130 and the coordinate conversion relationship for converting the coordinate from the third coordinate system 1220 of the patient marker 174 into the coordinate system of the tracking unit 130 may be created by using the positions and postures of the patient marker 174 and the imaging unit marker 170, which are measured by using the tracking unit 130.

The third coordinate conversion relationship for converting the coordinate from the third coordinate system 1220 of the patient marker 174 into the fourth coordinate system 1230 of the stereotactic surgery unit 1 may be created by using (i) the position and posture of a marker that is positioned at the origin of the stereotactic surgery unit 1 and (ii) the position and posture of the patient marker 174. At this time, the position and posture of each marker may be measured by using the tracking unit 130. Here, the origin of the stereotactic surgery unit 1 may be defined as an intersection point of the rotational axes of the stereotactic surgery unit 1. According to another embodiment, the third coordinate conversion relationship may be created through a geometric calculation (kinematic calculation) by using the fact that the position where the patient marker 174 is attached and the position of the origin of the stereotactic surgery unit 1 remain constant.

As described above, if the coordinate on the first coordinate system 1210 of the first imaging data are converted in sequence into: the coordinate on the third coordinate system 1220 of the patient marker 174; and then the coordinate on the fourth coordinate system 1230 of the stereotactic surgery unit 1, the position 1110 of a surgical target and the entry position 1130 of a surgical instrument, which are expressed with the coordinates on the first coordinate system 1210 of the first imaging data, may be converted into the fourth coordinate system 1230 of the stereotactic surgery unit 1. Meanwhile, if the patient 160 moves, the coordinate conversion relationships as described above may vary. Therefore, the patient 160 is required to be fixed without moving, and if the patient 160 moves, the controller 140 is to obtain the coordinate conversion relationships above again.

Figure 14:
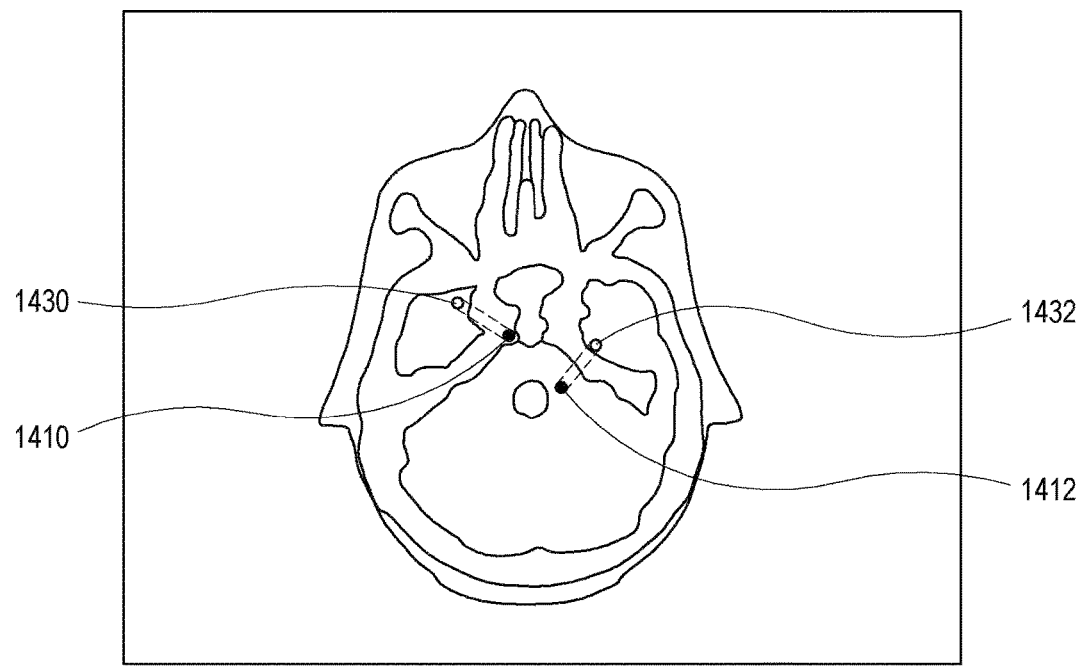
FIG. 14 is a view in which a user displays the position of a surgical target and the entry position of a surgical instrument in the two-dimensional sectional image on the axial plane of the three-dimensional image of the patient, which contains a surgical portion that is photographed prior to surgery, according to an embodiment of the present disclosure.
Figure 15:
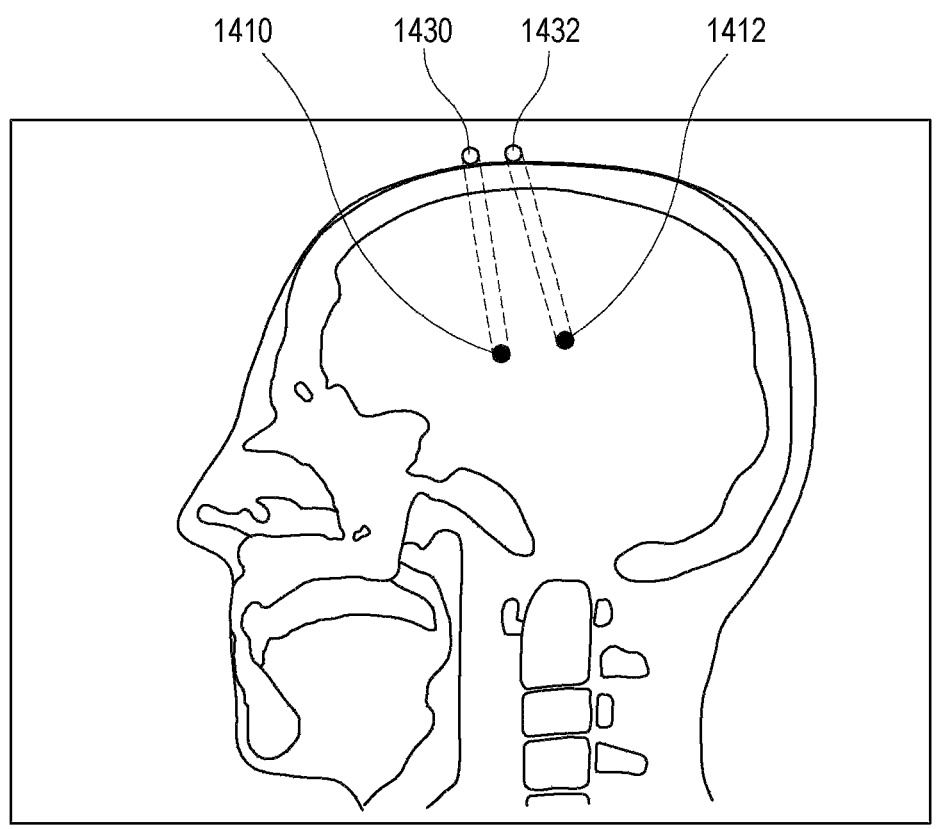
FIG. 15 is a view in which a user displays the position of a surgical target and the entry position of a surgical instrument in the two-dimensional and sectional image on the sagittal plane of the three-dimensional image of the patient, which contains a surgical portion that is photographed prior to surgery, according to an embodiment of the present disclosure.
Figure 16:
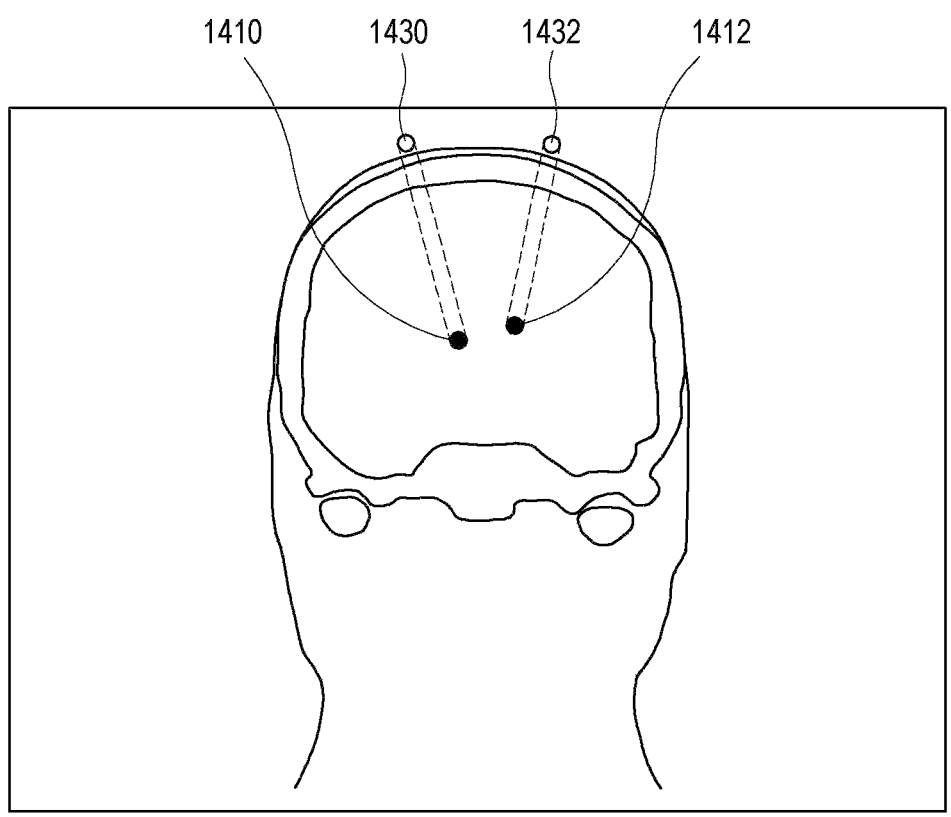
FIG. 16 is a view in which a user displays the position of a surgical target and the entry position of a surgical instrument in the two-dimensional and sectional image on the coronal plane of the three-dimensional image of the patient, which contains a surgical portion that is photographed prior to surgery, according to an embodiment of the present disclosure.

According to an embodiment, the stereotactic surgery unit 1 of the present disclosure may be controlled based on the position of a surgical target and/or the entry position of a surgical instrument, which are displayed on the two-dimensional sectional image that constitutes a three-dimensional image that is represented by the first imaging data. FIGS. 14 to 16 are two-dimensional sectional images on the axial plane, on the sagittal plane, and on the coronal plane of a surgical portion, respectively, which are photographed prior to surgery. The controller 140 may extract such two-dimensional sectional images from the first imaging data, and may visualize the same to the user through the user interface 150.

The user may display the position 1410 or 1412 of a surgical target and the entry position 1430 or 1432 of a surgical instrument on the two-dimensional sectional images that are visualized through the user interface 150. The controller 140 may convert the position 1410 or 1412 of a surgical target and/or the entry position 1430 or 1432 of a surgical instrument, which are displayed on the sixth coordinate system 1260 of the two-dimensional sectional image into the positions on the fourth coordinate system 1230 of the stereotactic surgery unit 1, and may then move the moving unit 10 according to the converted position of the surgical target. In addition, the controller 140 may rotate the rotating unit 40 to which the surgical instrument is attached such that the surgical instrument has the entry posture of a surgical instrument, which has been determined based on the converted position of a surgical target and the converted entry position of a surgical instrument.

Figure 12:
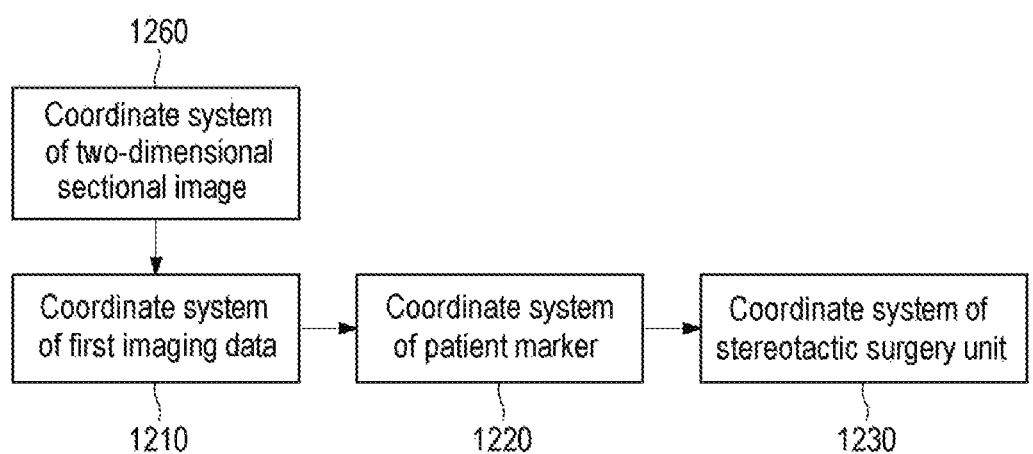
FIG. 12 is a view to explain a method for converting the position of a surgical target and the entry position of a surgical instrument, which are displayed on the three-dimensional image or the two-dimensional sectional image of the three-dimensional image that contains a surgical portion, into the positions on the coordinate system of a stereotactic surgery unit, according to an embodiment of the present disclosure.

As shown in FIG. 12, in order to convert the coordinates displayed on the sixth coordinate system 1260 of the two-dimensional sectional image into the coordinates on the fourth coordinate system 1230 of the stereotactic surgery unit 1, the coordinates on the sixth coordinate system 1260 of the two-dimensional sectional image may be converted in sequence into: (i) the coordinate on the first coordinate system 1210 of the first imaging data; (ii) the coordinate on the third coordinate system 1220 of the patient marker 174; and then (iii) the coordinate on the fourth coordinate system 1230 of the stereotactic surgery unit 1.

However, the second coordinate conversion relationship for converting the coordinate from the first coordinate system 1210 into the third coordinate system and the third coordinate conversion relationship for converting the coordinate from the third coordinate system into the fourth coordinate system may be created in advance through the embodiments described above. Therefore, when the user wishes to control the stereotactic surgery unit 1 through the two-dimensional sectional image that is displayed on the user interface 150, the stereotactic surgery unit 1 may be controlled by simply creating only a coordinate conversion relationship for converting the coordinate from the sixth coordinate system 1260 of the two-dimensional sectional image into the first coordinate system 1210 of the first imaging data.

According to an embodiment, since the two-dimensional sectional image may be created from the first imaging data, the coordinate conversion relationship for converting the coordinate from the sixth coordinate system 1260 of the two-dimensional sectional image into the first coordinate system 1210 of the first imaging data may be created based on such a created relationship.

Meanwhile, the controller 140 is required to recognize the initial position and posture of a surgical instrument prior to moving and/or rotating the surgical instrument attached to the stereotactic surgery unit 1. According to an embodiment, in order to recognize the position and posture of a surgical instrument, the stereotactic surgery unit marker 172 is attached to a portion near the surgical instrument in the rotating unit 40 of the stereotactic surgery unit 1, and the position and posture of the stereotactic surgery unit marker 172 may be measured by the tracking unit 130. However, the position and posture of the stereotactic surgery unit marker 172 refers to the position and posture on the coordinate system of the tracking unit 130. Therefore, the controller 140 may convert the position and posture of the stereotactic surgery unit marker 172 on the coordinate system of the tracking unit 130 into the position and posture on the fourth coordinate system 1230 of the stereotactic surgery unit 1, and may then recognize the initial position and posture of the surgical instrument based on the converted position and posture.

As described above, the control of the stereotactic surgery unit 1 of the present disclosure starts from the creation of a coordinate conversion relationship (the first coordinate conversion relationship) for converting the coordinate from the coordinate system of a CT or MRI image that is photographed prior to surgery into the coordinate system of an imaging unit image that is obtained by using the imaging unit 120. At this time, the coordinate conversion relationship may be simply created through an image registration between the two images. However, if the surgical portion moves due to the inevitable movement of the patient 160 or the movement of a configuration, such as the surgical portion fixing unit 90 of the stereotactic surgery unit 1, during the stereotactic surgery, all the conditions for the control of the stereotactic surgery unit 1 may be changed. In this case, the controller 140 is required to obtain the coordinate conversion relationships described above again. In the case of the present disclosure, even if such a movement occurs during the stereotactic surgery, once only the imaging data is again created through the imaging unit 120, the coordinate conversion relationships for controlling the stereotactic surgery unit 1 may be simply created again by using an image registration between an image that is represented by the imaging data and a CT or MRI image. Therefore, even with the movement of the patient 160 during the stereotactic surgery, the stereotactic surgery can be resumed within a short time.

In addition, in the prior art, since the position of the stereotactic surgery robot does not remain constant and the stereotactic surgery robot may move during surgery, the position of the surgical robot should be accurately recognized in order to control the operation of the surgical robot based on the current position of the surgical robot. To this end, according to the prior art, additional markers are attached to the base of the surgical robot, and the position of the surgical robot can be recognized by using the same. However, since the stereotactic surgery unit 1 of the present disclosure is used while being fixed to the operating table 110, a positional relationship between the stereotactic surgery unit 1 and the surgical portion may always be maintained to be constant, and the position of the stereotactic surgery unit 1 is not changed. Therefore, according to the surgical robot system 100 of the present disclosure, the conventional and additional markers are not required because the position for controlling the stereotactic surgery unit 1 does not need to be recognized, and accordingly, the amount of calculation for the control may be reduced.

Figure 17:
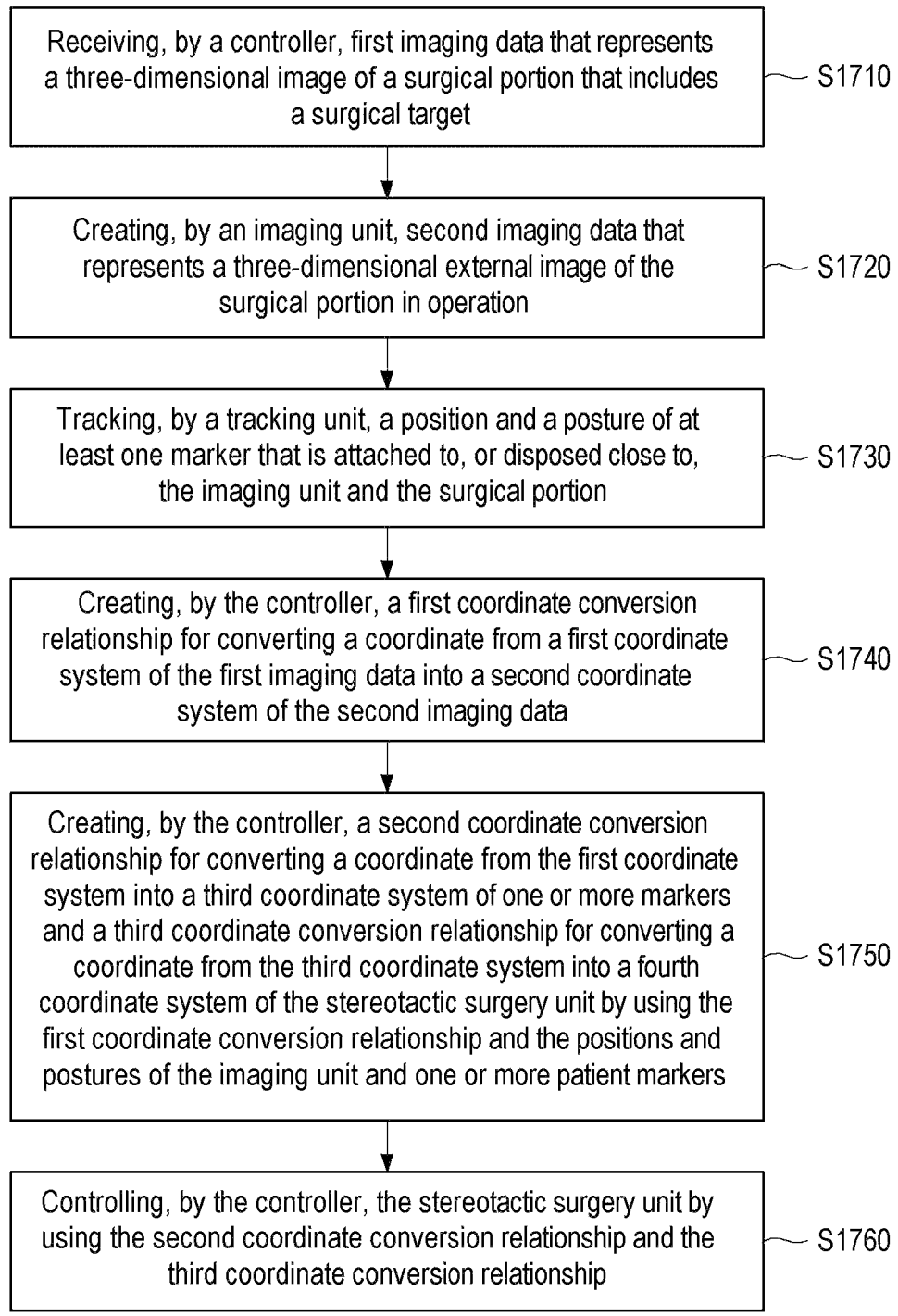
FIG. 17 is a flowchart showing a method for controlling a stereotactic surgery unit, according to an embodiment of the present disclosure.

FIG. 17 is a flowchart illustrating a method for controlling the stereotactic surgery unit that moves and rotates a surgical instrument at 5 degrees of freedom or more in the stereotactic surgery robot system, according to an embodiment of the present disclosure.

First, in operation S1710, the controller may receive first imaging data that represents a three-dimensional image of a surgical portion that includes a surgical target. For example, referring to FIG. 2, the controller 140 may receive, from the storage device 180, imaging data that represents a three-dimensional image for a surgical portion, which is photographed prior to surgery. The first imaging data may be visualized through the user interface 150 to then be used as data to determine the position of a surgical target and the entry position of a surgical instrument. When the position of a surgical target and the entry position of a surgical instrument are input through the user interface 150, the controller 140 may control the stereotactic surgery unit 1 based on the position of a surgical target and the entry position of a surgical instrument, which are input.

After the controller 140 receives the first imaging data in operation S1710, the imaging unit may create second imaging data that represents a three-dimensional external image of the surgical portion in operation S1720. For example, the imaging unit 120 may create the second imaging data that represents a three-dimensional image of the position in which the surgical instrument passes through a skull. According to an embodiment, the second imaging data may be created by Phase Measuring Profilometry using a pattern light, etc.

After the first and second imaging data are prepared through operations S1710 and S1720, the tracking unit may track the position and posture of at least one marker that is attached to, or disposed close to, the imaging unit and the surgical portion in operation S1730. For example, referring to FIG. 2, the tracking unit 130 may track the position and posture of the imaging unit 120 by tracking the marker 170 that is attached to the imaging unit 120. In addition, the tracking unit 130 may track the position and posture of the patient marker 174. Meanwhile, since operations S1710 to S1730 are intended for the controller 140 to obtain data for controlling the stereotactic surgery unit 1, the sequence of the operations may be changed, and the operations may be performed in parallel.

After the data for the control of the stereotactic surgery unit 1 is prepared as described above, in operation S1740, the controller may create the first coordinate conversion relationship for converting a coordinate from the first coordinate system of the first imaging data into the second coordinate system of the second imaging data. According to an embodiment, the operation in which the controller 140 creates the first coordinate conversion relationship may include an operation in which the controller 140 creates the first coordinate conversion relationship through an image registration between a three-dimensional image represented by the first imaging data and a three-dimensional image represented by the second imaging data. According to an embodiment, the controller 140 may perform the image registration by using at least a portion of the surgical portion that is commonly included in the three-dimensional image represented by the first imaging data and the three-dimensional image represented by the second imaging data.

After the first coordinate conversion relationship is created in operation S1740, in operation S1750, the controller may create the second coordinate conversion relationship for converting the coordinate from the first coordinate system into the third coordinate system of one or more markers and the third coordinate conversion relationship for converting the coordinate from the third coordinate system into the fourth coordinate system of the stereotactic surgery unit by using the first coordinate conversion relationship and the positions and postures of the imaging unit and one or more patient markers. For example, referring to FIG. 12, the controller 140 may create the second coordinate conversion relationship for converting the coordinate from the first coordinate system 1210 of the first imaging data into the third coordinate system 1220 of the patient marker 174 and the third coordinate conversion relationship for converting the coordinate from the third coordinate system 1220 of the patient marker 174 into the fourth coordinate system 1230 of the stereotactic surgery unit 1.

Figure 18:
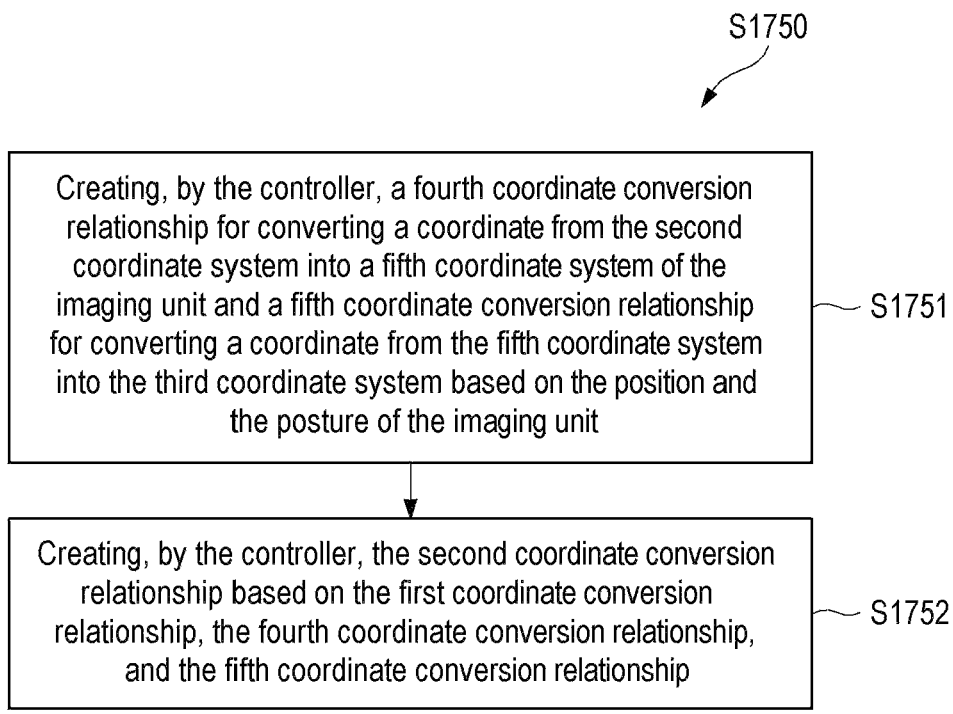
FIG. 18 is a flowchart showing a method for creating a coordinate conversion relationship for converting a coordinate from the coordinate system of imaging data representing the three-dimensional image that contains a surgical portion into the coordinate system of a patient marker, according to an embodiment of the present disclosure.

According to an embodiment, the controller 140 may create the second coordinate conversion relationship based on the position and posture of the imaging unit 120. More specifically referring to FIG. 18, in operation S1751, the controller may create the fourth coordinate conversion relationship for converting the coordinate from the second coordinate system into the fifth coordinate system of the imaging unit and the fifth coordinate conversion relationship for converting the coordinate from the fifth coordinate system into the third coordinate system based on the position and posture of the imaging unit. For example, referring to FIG. 13, the controller 140 may create the fourth coordinate conversion relationship for converting the coordinate from the second coordinate system 1240 of the second imaging data into the fifth coordinate system 1250 of the imaging unit 120 and the fifth coordinate conversion relationship for converting the coordinate from the fifth coordinate system 1250 of the imaging unit 120 into the third coordinate system 1220 of the patient marker 174 based on the position and posture of the imaging unit 120.

According to an embodiment, the fourth coordinate conversion relationship may be created by using (i) the coordinate conversion relationship for converting the coordinate from the reference coordinate system of the optical system of the imaging unit 120 into the fifth coordinate system 1250 of the imaging unit 120 and (ii) the coordinate conversion relationship for converting the coordinate from the second coordinate system 1240 of the second imaging data into the reference coordinate system of the optical system of the imaging unit 120. According to an embodiment, the fifth coordinate conversion relationship may be created by using (i) the coordinate conversion relationship for converting the coordinate from the fifth coordinate system 1250 of the imaging unit 120 into the coordinate system of the tracking unit 130 and (ii) the coordinate conversion relationship for converting the coordinate from the third coordinate system 1220 of the patient marker 174 into the coordinate system of the tracking unit 130.

When the fourth coordinate conversion relationship and the fifth coordinate conversion relationship are created, in operation S1752, the controller 140 may create the second coordinate conversion relationship based on the first coordinate conversion relationship, the fourth coordinate conversion relationship, and the fifth coordinate conversion relationship. According to an embodiment, such a coordinate conversion relationship may be expressed in the form of a coordinate conversion matrix. Therefore, the second coordinate conversion relationship may be created through a calculation by using a matrix showing the first coordinate conversion relationship, a matrix showing the fourth coordinate conversion relationship, and a matrix showing the fifth coordinate conversion relationship, which are created.

According to an embodiment, the third coordinate conversion relationship may be created by using (i) the position and posture of a marker that is positioned at the origin of the stereotactic surgery unit 1 and (ii) the position and posture of at least one marker (patient marker), which may be obtained by using the tracking unit 130. According to another embodiment, the third coordinate conversion relationship may be created through a geometric calculation (kinematic calculation) by using the fact that the position where the patient marker 174 is attached and the position of the origin of the stereotactic surgery unit 1 remain constant.

After the second coordinate conversion relationship and the third coordinate conversion relationship are created as described above, in operation S1760, the controller may control the stereotactic surgery unit by using the second coordinate conversion relationship and the third coordinate conversion relationship. More specifically, the description will be made hereinafter with reference to FIG. 19. When the second coordinate conversion relationship and the third coordinate conversion relationship are created through operations S1710 to S1750, the controller may visualize the first imaging data through the user interface in order for the user to input the position of a surgical target and the entry position of a surgical instrument in operation S1761. For example, referring to FIG. 2, the controller 140 may visualize the first imaging data that represents a three-dimensional image of a surgical portion including a surgical target through the user interface 150.

When the visualization of the first imaging data is made through operation S1761, the position of a surgical target and the entry position of a surgical instrument may be input through the user interface 150 to then be displayed on the visualized image. The controller may convert the position of a surgical target and the entry position of a surgical instrument, which have been input by the user through the user interface, into the coordinates on the first coordinate system. For example, referring to FIG. 2, the controller 140 may convert the position of a surgical target and the entry position of a surgical instrument, which have been input by the user through the user interface 150, into the coordinates on the first coordinate system 1210 of the first imaging data.

When the position of a surgical target and the entry position of a surgical instrument, which have been input through the user interface 150, are converted into the coordinates on the first coordinate system 1210 as described above, in operation S1763, the controller may convert the converted coordinates on the first coordinate system into the coordinates on the fourth coordinate system of the stereotactic surgery unit by using the second coordinate conversion relationship and the third coordinate conversion relationship. For example, referring to FIG. 12, the controller 140 may convert the coordinate of a surgical target and the coordinate of the entry position of a surgical instrument on the first coordinate system 1210 of the first imaging data into the coordinates on the fourth coordinate system 1230 of the stereotactic surgery unit 1 by using the second coordinate conversion relationship and the third coordinate conversion relationship.

After the coordinate of a surgical target and the coordinate of the entry position of a surgical instrument on the first coordinate system 1210 of the first imaging data are converted into the coordinates on the fourth coordinate system 1230 of the stereotactic surgery unit 1 as described above, in operation S1764, the controller may determine the entry posture of a surgical instrument based on the coordinates on the fourth coordinate system that is converted. For example, the controller 140 may determine the entry posture of a surgical instrument such that the surgical instrument moves from the entry position of the surgical instrument to the position of the surgical target.

Thereafter, in operation S1765, the controller may move the rotating unit through the moving unit such that the coordinate corresponding to the position of a surgical target on the fourth coordinate system are positioned at the intersection point of two rotational axes of the rotating unit. For example, referring to FIGS. 4 and 5, the controller 140 may move the rotating unit 40 that is attached to the moving unit 10 through the moving unit 10 such that the coordinate corresponding to the position of a surgical target are positioned at the intersection point of two rotational axes 43 and 45 of the rotating unit 40 on the fourth coordinate system 1230 of stereotactic surgery unit 1.

In addition, the controller may rotate the surgical instrument through the rotating unit such that the surgical instrument has the determined entry posture of the surgical instrument in operation S1766. For example, referring to FIG. 5, the controller 140 may rotate the surgical instrument 50 that is attached to the rotating unit 40 through the rotating unit 40 such that the surgical instrument 50 has the determined entry posture of the surgical instrument 50. As described above, the controller 140 of the present disclosure may independently control the moving unit 10 and the rotating unit 40, respectively.

Although the method has been described through specific embodiments, the method may also be implemented as a computer-readable code in a computer-readable recording medium. The computer-readable recording medium includes all kinds of recording devices that store data that can be read by a computer system. The examples of the computer-readable recording medium may include ROM, RAM, CD-ROM, magnetic tapes, floppy disks, optical data storage devices, or the like, or may be implemented in the form of a carrier wave (for example, the transmission through the Internet). In addition, the computer-readable recording medium may be distributed to computer systems that are connected through a network, and a computer-readable code may be stored and executed in a distributed manner. In addition, functional programs, codes, and code segments for implementing the embodiments may be easily inferred by the programmers who are skilled in the art.

Although embodiments of disclosure have been described, it should be noted that there may be various modifications and changes without departing from the spirit and scope of the present disclosure, which can be understood by those skilled in the art. In addition, such modifications and changes should be considered to be within the scope of the claims appended herein.

What is claimed is:

1. A stereotactic surgery robot comprising:
    a rotating unit configured to have a surgical instrument that is able to be attached thereto, and configured to rotate the surgical instrument on at least one of two rotational axes according to an entry posture of the surgical instrument;
    a moving unit configured to move the rotating unit in a direction of at least one of three linear axes according to a position of a surgical target; and
    a surgical portion support unit configured to be connected to the moving unit, and configured to be detachable with respect to an operating table,
    wherein the moving unit moves the rotating unit such that an intersection point of the two rotational axes matches the surgical target, wherein the moving unit comprises:
    wherein the moving unit comprises: a first direction driving unit configured to move along a first linear axial direction; a second direction driving unit configured to move along a second linear axial direction while being connected to the first direction driving unit; and a third direction driving unit configured to move along a third linear axial direction while being connected to the second direction driving unit, and wherein the rotating unit comprises: a first rotational driving unit configured to rotate on a first rotational axis of the at least two rotational axes, while one end of the first rotational driving unit is connected to the third direction driving unit; and a second rotational driving unit configured to rotate on a second rotational axis of the at least two rotational axes, while one end of the second rotational driving unit is connected to the other end of the first rotational driving unit and while the surgical instrument is attached to the other end of the second rotational driving unit.

2. The stereotactic surgery robot according to claim 1, wherein the surgical portion support unit comprises a connecting unit that is detachably connected to the moving unit.

3. The stereotactic surgery robot according to claim 2, wherein the surgical portion support unit further comprises:
    an angle adjusting unit configured to adjust the angle of the surgical portion support unit; and
    a posture adjusting unit configured to include a height adjusting unit for adjusting the height of the surgical portion support unit.

4. The stereotactic surgery robot according to claim 3, wherein the surgical portion support unit further comprises an operating table fixing unit configured to detachably fix a posture adjusting unit to the operating table while being connected to the posture adjusting unit.

5. The stereotactic surgery robot according to claim 4, further comprising a surgical portion fixing unit configured to be fixedly disposed in the surgical portion support unit and configured to fix the surgical portion support unit to prevent the movement of the surgical portion support unit.

6. The stereotactic surgery robot according to claim 5, wherein the surgical portion fixing unit comprises a surgical portion fixing frame and a surgical portion fixing pin, and wherein the surgical portion fixing frame is configured in a shape to prevent the surgical portion fixing frame from blocking a feature region when an imaging unit forms an image of the feature region of the surgical portion support unit.

7. The stereotactic surgery robot according to claim 6, further comprising an insulating unit configured to be interposed between the surgical portion fixing frame and the surgical portion support unit.

8. The stereotactic surgery robot according to claim 1, wherein the first to third linear axial directions are perpendicular to each other, and the first rotational axis and the second rotational axis are perpendicular to each other.

9. The stereotactic surgery robot according to claim 1, wherein a holder to which the surgical instrument is detachably attached is attached to the other end of the second rotational driving unit.

10. The stereotactic surgery robot according to claim 9, wherein a surgical instrument detecting unit for detecting a mounting of the surgical instrument is further attached to the other end of the second rotational driving unit.

11. The stereotactic surgery robot according to claim 1, wherein the third direction driving unit has a hole centered on the first rotational axis.

* * * * *